(12) United States Patent
Sands et al.

(10) Patent No.: US 6,509,027 B2
(45) Date of Patent: Jan. 21, 2003

(54) INJECTABLE PHARMACEUTICAL COMPOSITION COMPRISING COATED PARTICLES OF CAMPTOTHECIN

(75) Inventors: Howard Sands, Wilmington, DE (US); Awadhesh Mishra, Quebec (CA)

(73) Assignees: SuperGen, Inc., Dublin, CA (US); RTP Pharma Inc., Quebec (CA)

(*) Notice: Subject to any disclaimer, the term of this patent is extended or adjusted under 35 U.S.C. 154(b) by 0 days.

(21) Appl. No.: 09/782,168

(22) Filed: Feb. 12, 2001

(65) Prior Publication Data
US 2002/0142048 A1 Oct. 3, 2002

(51) Int. Cl.[7] .............. A61F 2/02; A61K 9/127
(52) U.S. Cl. ................. 424/423; 424/450
(58) Field of Search .................. 424/423, 450

(56) References Cited

U.S. PATENT DOCUMENTS

| | | | |
|---|---|---|---|
| 4,622,219 A | 11/1986 | Haynes | 424/38 |
| 4,663,161 A | 5/1987 | Mannino et al. | 424/89 |
| 4,725,442 A | 2/1988 | Haynes | 424/490 |
| 5,043,165 A | 8/1991 | Radhakrishnan | 424/450 |
| 5,077,057 A | 12/1991 | Szoka, Jr. | 424/450 |
| 5,091,187 A | 2/1992 | Haynes | 424/450 |
| 5,091,188 A | 2/1992 | Haynes | 424/450 |
| 5,145,684 A | 9/1992 | Liversidge et al. | 424/489 |
| 5,399,363 A | 3/1995 | Liversidge et al. | 424/490 |
| 5,439,686 A | 8/1995 | Desai et al. | 424/451 |
| 5,494,683 A | 2/1996 | Liversidge et al. | 424/490 |
| 5,503,723 A | 4/1996 | Ruddy et al. | 204/450 |
| 5,549,910 A | 8/1996 | Szoka, Jr. | 424/450 |
| RE35,338 E | 9/1996 | Haynes | 424/450 |
| 5,552,156 A | 9/1996 | Burke | 424/450 |
| 5,560,933 A | 10/1996 | Soon-Shiong et al. | 424/489 |
| 5,565,188 A | 10/1996 | Wong et al. | 424/9.411 |
| 5,631,237 A | 5/1997 | Dzau et al. | 514/44 |
| 5,718,914 A | 2/1998 | Foldvari | 424/450 |
| 5,736,156 A | 4/1998 | Burke | 424/450 |
| 5,776,486 A | 7/1998 | Castor et al. | 424/450 |
| 5,783,211 A | 7/1998 | Manzo et al. | 424/450 |
| 5,827,533 A | 10/1998 | Needham | 424/450 |
| 5,834,012 A | 11/1998 | Perez-Soler et al. | 424/450 |
| 5,874,105 A | 2/1999 | Watkins et al. | 424/450 |
| 5,882,679 A | 3/1999 | Needham | 424/450 |
| 6,027,726 A | 2/2000 | Ansell | 424/180.1 |
| 6,056,973 A | 5/2000 | Allen et al. | 424/450 |
| 6,090,407 A | 7/2000 | Knight et al. | 424/450 |
| 6,096,336 A | 8/2000 | Cao et al. | 424/450 |
| 6,133,416 A | 10/2000 | Wilson et al. | 530/300 |
| 6,136,978 A | 10/2000 | Curran et al. | 546/14 |
| 6,143,321 A | 11/2000 | Needham et al. | 424/450 |
| 6,197,333 B1 | 3/2001 | Onyuksel et al. | 424/450 |
| 6,217,886 B1 | 4/2001 | Önyüksel | 424/401 |
| 6,228,855 B1 | 5/2001 | Cao et al. | 514/224.12 |
| 6,291,425 B1 * | 9/2001 | Li et al. | 514/8 |
| 6,291,676 B1 | 9/2001 | Burke et al. | 546/48 |
| 6,296,870 B1 | 10/2001 | Needham et al. | 424/450 |

\* cited by examiner

Primary Examiner—Carlos Azpuru
(74) Attorney, Agent, or Firm—U. P. Peter Eng; Wilson Sonsini Goodrich & Rosati

(57) ABSTRACT

A pharmaceutical composition is provided which comprises an aqueous suspension of solid particles, the solid particles comprising a camptothecin, the solid particles having mean diameters between about 0.05 um and 10 um, the particles coated with a 0.3 nm to 3.0 um thick layer of a membrane-forming amphipathic lipid. The pharmaceutical composition is particularly well suited for delivering camptothecins, particularly 9-nitro-camptothecin intravenously.

38 Claims, 19 Drawing Sheets

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|
| Sample Identification | 9-Nitrocamptothecin (g) | Lipoid E80 (g) | Mannitol (g) | Trehalose (g) | Water (g) | Aq. Na Acetate* (g) | Batch size (g) | Diluent** | Dilution Factor | 9-Nitrocamptothecin Concentration, mg/g | Lipoid E80 Concentration, mg/g | Mannitol Concentration, mg/g | Trehalose Concentration, mg/g | pH | Mean Size*** (µm) | Size:99.9%**** (µm) |
| 1-A | 0.252 | 1.051 | 2.74 | | 41.5 | 5.0 | 50.6 | MAN | 2.5 | 1.99 | 8.3 | 55.0 | | 5.6 | 1.93 | 6.52 |
| 1-B | 0.253 | 1.001 | 2.75 | | 41.1 | 5.0 | 50.1 | MAN | 2.5 | 2.02 | 8.0 | 55.0 | | 5.7 | 1.02 | 2.47 |
| 1-C | 0.250 | 2.001 | 2.76 | | 40.0 | 5.0 | 50.0 | MAN | 2.5 | 2.00 | 16.0 | 55.0 | | 5.8 | 0.96 | 2.44 |
| 1-D | 0.259 | 2.510 | | 6.0 | 36.3 | 5.0 | 50.0 | TRE | 2.5 | 2.07 | 20.1 | | 120.0 | 5.9 | 0.15 | 0.87 |
| 1-Ea | 0.250 | 5.000 | | 6.0 | 33.8 | 5.0 | 50.1 | TRE | 2.5 | 2.00 | 40.0 | | 121.3 | 6.0 | 0.07 | 0.22 |
| 1-Eb | | | | | | | | TRE | 2.5 | 2.00 | 40.0 | | 241.3 | 6.0 | 0.07 | 0.20 |
| 1-Ec | | | | | | | | TRE | 2.5 | 2.00 | 40.0 | | 361.3 | 6.0 | 0.27 | 2.00 |
| 1-F | 1.256 | 25.1 | | 15.0 | 71.5 | 12.5 | 125.4 | TRE | 5.0 | 2.00 | 40.0 | | 240.5 | 5.0 | 1.29 | 2.80 |
| 1-V | | 16.0 | | 9.6 | 46.4 | 8.0 | 80.0 | TRE | 5.0 | | 4.0 | | 239.7 | 4.8 | 0.07 | 0.01 |

Examples of aqueous suspension compositions containing micrometer or submicrometer size particles of 9-nitrocamptothecin suitable for intravenous injection.

\* Aq. Na Acetate: 20 mM sodium acetate solution in water with sodium hydroxide added to adjust pH to 5.0.
\*\* Diluent: Aqueous solution containing mannitol (MAN) or trehalose (TRE) and sodium acetate in sufficient quantity to give the final concentration of sodium acetate of 2 mM and that of other ingredients as shown in columns 11-14 of Table 1.
\*\*\* Mean Size: Volume weighted mean particle diameter ($D_{4,3}$) in micrometers determined by a Malvern Mastersizer Microplus apparatus.
\*\*\*\* Size:99.9%: 99.9% of the particle population is smaller than this volume weighted particle diameter as determined by a Malvern Mastersizer Microplus apparatus.

FIGURE 1

Examples of aqueous suspension compositions containing micrometer or submicrometer size particles of 9-nitrocamptothecin suitable for intravenous injection.

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|
| Sample Identification | 9-Nitrocamptothecin (g) | Lipoid E80 (g) | Mannitol (g) | Trehalose (g) | Water (g) | Aq. Na Acetate* (g) | Batch size (g) | Diluent** | Dilution Factor | 9-Nitrocamptothecin Concentration, mg/g | Lipoid E80 Concentration, mg/g | Mannitol Concentration, mg/g | Trehalose Concentration, mg/g | pH | Mean Size*** ($\mu$m) | Size: 99.9%**** ($\mu$m) |
| 1-A | 0.252 | 1.051 | 2.74 |  | 41.5 | 5.0 | 50.6 | MAN** | 2.5 | 1.99 | 8.3 | 55.0 |  | 5.6 | 1.93 | 6.52 |
| 1-B | 0.253 | 1.001 | 2.75 |  | 41.1 | 5.0 | 50.1 | MAN | 2.5 | 2.02 | 8.0 | 55.0 |  | 5.7 | 1.02 | 2.47 |
| 1-C | 0.250 | 2.001 | 2.76 |  | 40.0 | 5.0 | 50.0 | MAN | 2.5 | 2.00 | 16.0 | 55.0 |  | 5.8 | 0.96 | 2.44 |
| 1-D | 0.259 | 2.510 |  | 6.0 | 36.3 | 5.0 | 50.0 | TRE** | 2.5 | 2.07 | 20.1 |  | 120.0 | 5.9 | 0.15 | 0.87 |
| 1-Ea | 0.250 | 5.000 |  | 6.0 | 33.8 | 5.0 | 50.1 | TRE | 2.5 | 2.00 | 40.0 |  | 121.3 | 6.0 | 0.07 | 0.22 |
| 1-Eb |  |  |  |  |  |  |  | TRE | 2.5 | 2.00 | 40.0 |  | 241.3 | 6.0 | 0.07 | 0.20 |
| 1-Ec |  |  |  |  |  |  |  | TRE | 2.5 | 2.00 | 40.0 |  | 361.3 | 6.0 | 0.27 | 2.00 |
| 1-F | 1.256 | 25.1 |  | 15.0 | 71.5 | 12.5 | 125.4 | TRE | 5.0 | 2.00 | 40.0 |  | 240.5 | 5.0 | 1.29 | 2.80 |
| 1-V |  | 16.0 |  | 9.6 | 46.4 | 8.0 | 80.0 | TRE | 5.0 |  | 4.0 |  | 239.7 | 4.8 | 0.07 | 0.01 |

\*      Aq. Na Acetate:     20 mM sodium acetate solution in water with sodium hydroxide added to adjust pH to 5.0.

\*\*     Diluent                 Aqueous solution containing mannitol (MAN) or trehalose (TRE) and sodium acetate in sufficient quantity to give the final concentration of sodium acetate of 2 mM and that of other ingredients as shown in columns 11-14 of Table 1.

\*\*\*    Mean Size            Volume weighted mean particle diameter ($D_{4,3}$) in micrometers determined by a Malvern Mastersizer Microplus apparatus.

\*\*\*\*   Size:99.9%          99.9% of the particle population is smaller than this volume weighted particle diameter as determined by a Malvern Mastersizer Microplus apparatus.

FIGURE 2

| Stability of an aqueous suspension formulation of 9-nitrocamptothecin stored at 4°C, 25°C, and 40°C for up to 170 days. | | | |
|---|---|---|---|
| Storage Temperature and Duration | Volume weighted particle diameter, micrometers | | Appearance |
| | Mean | 99.9 percentile | |
| Initial | 1.29 | 2.80 | Homogeneous yellow suspension, crystalline particles were observed in optical microscope under polarized light with a size distribution consistent with the measured size. |
| Stored at 4°C for 170 days | 1.27 | 3.00 | Small amounts of sediments were observed in the vial that were easily resuspendible to a homogeneous yellow suspension. Crystalline particles were observed in optical microscopic examination under polarized light with a size distribution consistent with the measured size. No agglomerates were found |
| Stored at 25°C for 170 days | 1.20 | 2.91 | |
| Stored at 40°C for 170 days | 1.31 | 4.78 | |

FIGURE 3

| IDD-D particle diameters in micrometers as a function of stress conditions. | | | | | | |
|---|---|---|---|---|---|---|
| | Initial Particle Size | 1. Stress Condition | | | | |
| | | Storage at 2-8°C | Storage at 20°C | Storage at 40°C | 4-40°C Cycling | Shaking |
| Test Duration | Day 0 | Day18 | Day18 | Day18 | Cycle3 | Day3 |
| Mean (volume weighted) | 0.20 μm | 0.19 μm | 0.18 μm | 0.17 μm | 0.19 μm | 0.20 μm |
| 99.9 Percentile | 0.34 μm | 0.34 μm | 0.31 μm | 0.31 μm | 0.33 μm | 0.33 μm |

FIGURE 4

Protocol Design For First Melanoma Xenograft Study

| Group | n | Treatment Regimen | | | |
|---|---|---|---|---|---|
| | | Agent | mg/kg | Route | Schedule |
| 1 | 10 | NoTreatment | n/a | n/a | |
| 2 | 10 | IDD-P(1:3dilution) | n/a | iv | 5/2/5 |
| 3 | 10 | IDD-D(nodilution) | n/a | iv | 5/2/5 |
| 4 | 10 | D5Wwith3%DMA | n/a | po | Day1,4,8,11 |
| 5 | 10 | CAMPTOSAR | 100 | ip | QWKx3 |
| 6 | 10 | HYCAMTIN | 10 | ip | Q4Dx4 |
| 7 | 10 | DTIC | 150 | ip | QDx5 |
| 8 | 10 | 9NC-IDD-P | 3 | iv | 5/2/5 |
| 9 | 10 | 9NC-IDD-P | 1.5 | iv | 5/2/5 |
| 10 | 10 | 9NC-IDD-D | 2 | iv | 5/2/5 |
| 11 | 10 | 9NC-IDD-D | 1 | iv | 5/2/5 |
| 12 | 10 | 9NC-D5W-3%DMA | 4 | po | Day1,4,8,11 |
| 13 | 10 | 9NC-D5W-3%DMA | 2 | po | Day1,4,8,11 |

FIGURE 5

Treatment Response Summary For First Melanoma Xenograft Study

| Group | n | Treatment Regimen | | | | MDSto2.0g ±SEM(n) | Max.%BW Loss;Day | #Death[a] | | #CR | #PR | #SD/PD |
|---|---|---|---|---|---|---|---|---|---|---|---|---|
| | | Agent | mg/kg | Route | Schedule | | | TR | NTR | | | |
| 1 | 10 | NoTreatment | n/a | n/a | | 30.3 ± 4.4 (9) | --- | 0 | 0 | 0 | 0 | 1 |
| 2 | 10 | IDD-P(1:3dilution) | n/a | iv | 5/2/5 | 29.2 ± 2.5 (10) | --- | 0 | 0 | 0 | 0 | 0 |
| 3 | 10 | IDD-D(nodilution) | n/a | iv | 5/2/5 | 31.6 ± 3.2 (10) | -0.4%;Day27 | 0 | 0 | 0 | 0 | 0 |
| 4 | 10 | D5Wwith3%DMA | n/a | po | Day1,4,8,11 | 26.0 ± 2.3 (8) | --- | 0 | 1 | 1 | 0 | 0 |
| 5 | 10 | CAMPTOSAR | 100 | ip | QWKx3 | 47.3 ± 2.3 (9) | --- | 0 | 0 | 1 | 0 | 0 |
| 6 | 10 | HYCAMTIN | 10 | ip | Q4Dx4 | 46.7 ± 2.6 (9) | --- | 0 | 0 | 1 | 0 | 0 |
| 7 | 10 | DTIC | 150 | ip | QDx5 | 37.6 ± 4.0 (8) | -5.2%;Day5 | 1 | 0 | 1 | 0 | 1 |
| 8 | 10 | 9NC-IDD-P | 3 | iv | 5/2/5 | 52.0 ± 0.6 (2) | -13.1%;Day13 | 3 | 0 | 1 | 3 | 1 |
| 9 | 10 | 9NC-IDD-P | 1.5 | iv | 5/2/5 | 50.7 ± 3.4 (7) | -2.2%;Day5 | 0 | 0 | 2 | 0 | 0 |
| 10 | 10 | 9NC-IDD-D | 2 | iv | 5/2/5 | 47.2 ± 3.6 (8) | --- | 0 | 0 | 1 | 1 | 0 |
| 11 | 10 | 9NC-IDD-D | 1 | iv | 5/2/5 | 32.6 ± 2.3 (10) | --- | 0 | 0 | 0 | 0 | 0 |
| 12 | 10 | 9NC-D5W-3%DMA | 4 | po | Day1,4,8,11 | 45.3 ± 7.0 (3) | --- | 0 | 0 | 4 | 0 | 3 |
| 13 | 10 | 9NC-D5W-3%DMA | 2 | po | Day1,4,8,11 | 47.6 ± 3.4 (3) | --- | 0 | 0 | 4 | 1 | 2 |

[a]#Death:TR(TreatmentRelated);NTR(Non-TreatmentRelated)

FIGURE 11

| Treatment | Mean (days) | +/_ SEM | P vs no treatment | Initial n/n reaching 2 g or surviving to day 62 |
|---|---|---|---|---|
| No treatment | 20.5 | 3.0 | --- | 10/10 |
| IDD-P vehicle iv (5/2/5) | 17.3 | 3.6 | 0.32 | 10/10 |
| IDD-D vehicle iv (5/2/5) | 18.0 | 5.4 | 0.48 | 10/10 |
| D5W with DMA (5/2/5) | 15.2 | 1.0 | 0.12 | 10/9 |
| Camptosar 100mg/kg ip (Qwkx3) | 39.7 | 3.2 | 0.0004 | 10/10 |
| Hycamtin 10 mgkg ip (Q4Dx4) | 39.9 | 2.9 | 0.0002 | 10/10 |
| DTIC 150 mg/kg ip (QDx5) | 31.3 | 4.6 | 0.06 | 10/9 |
| 9NC-in IDD-P 3 mg/kg iv | 56.2 | 3.1 | <<<0.0005 | 10/7 |
| 9NC in IDD-P 1.5 mg/kg iv | 45.5 | 3.7 | <<<0.0005 | 10/10 |
| 9NC in IDD-D 2mg/kg iv | 41.9 | 3.1 | <<<0.0005 | 10/10 |
| 9NC in IDD-D 1 mg/kg iv | 26.1 | 1.4 | 0.11 | 10/10 |
| 9NC 4 mg/kg oral | 54.1 | 3.8 | <<<0.0005 | 10/10 |
| 9NC 2 mg/kg oral | 54.6 | 3.1 | <<<0.0005 | 10/10 |

5/2/5 + 5 daily dose, 2 days rest, 5 daily
Qwkx3 one dose per week for 3 weeks
Q4Dx4 four doses per day at four day intervals
QDx5 one dose per day for 5 days

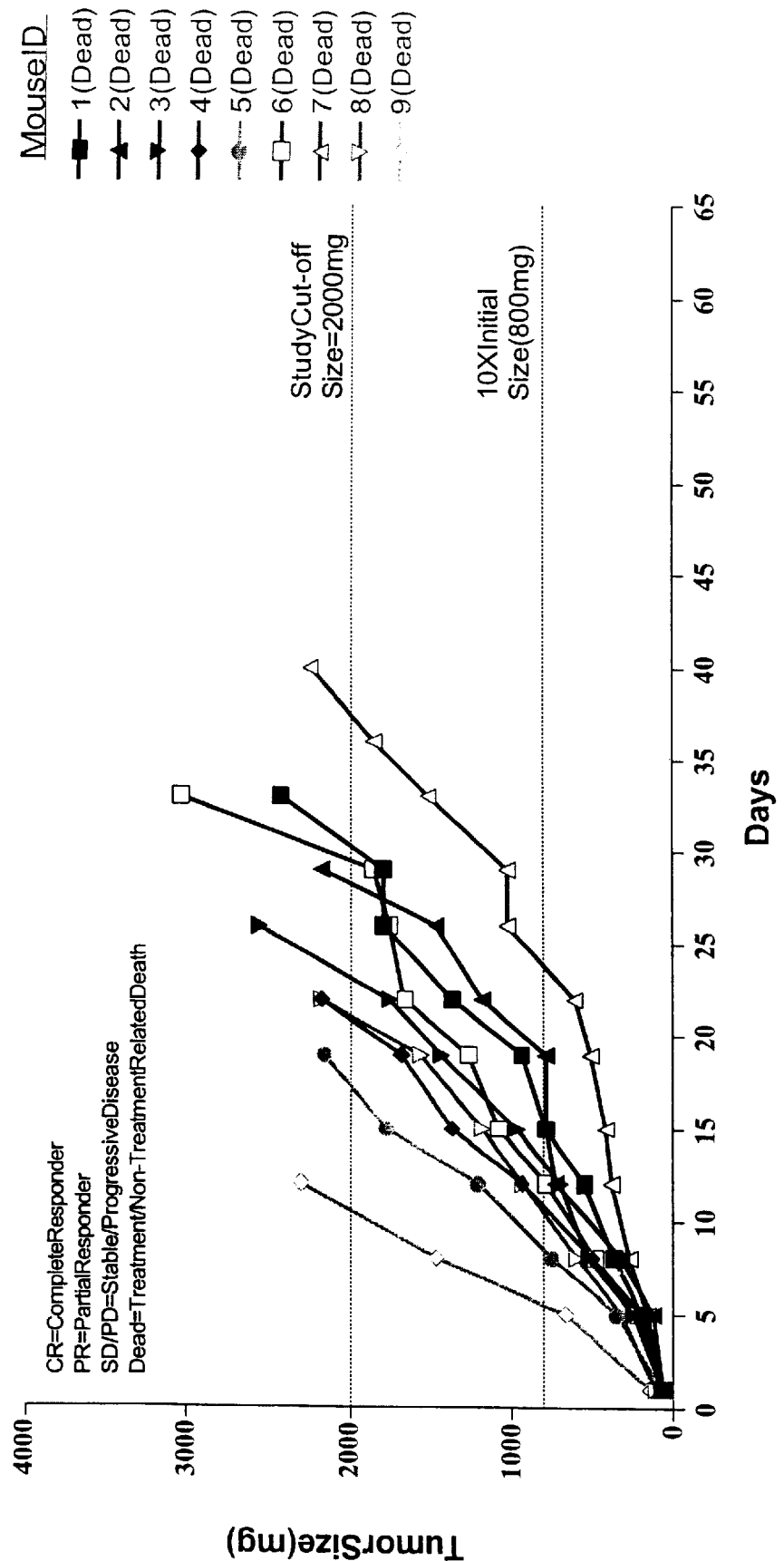

Group 2 of Second Melanoma Study

Group 3 of Second Melanoma Study

Group 5 of Second Melanoma Study

FIGURE 13

MX-1 Human Breast Cancer Xenograft Study

| Treatment | Schedule | Mean Days to 10 X | S.E.M | P vs. no treatment | # of mice at start/ # mice reaching 10x |
|---|---|---|---|---|---|
| No treatment | | 17.4 | 2.23 | -- | 10/10 |
| IDD-P vehicle i.v. | 5/2/5 | 16.5 | 1.1 | n.s | 10/10 |
| 9NC in IDDP 2.5 mg/kg i.v. | 5/2/5 | 53.0 | 0.0 | <<0.05 | 10/10 |
| 9NC in IDDP 1.75 mg/kg i.v. | 5/2/5 | 53.0 | 0.0 | <<0.05 | 10/10 |
| 9NC in IDDP 1.25 mg/kg i.v. | 5/2/5 | 47.5 | 2.1 | <<0.05 | 10/10. |
| Camptosar 100 mg/kg i.p.. | QWK x 3 | 53.0 | 0.0 | <<0.05 | 10/10 |
| Hycamtin 10 mg/kg i.p. | Q4D x 4 | 53.0 | 0.0 | <<0.05 | 10/10 |

FIGURE 14

Pan 1- Human Pancreatic Cancer Xenograft Study

| Treatment | Schedule | Mean Days to 10 X | S.E.M | P vs. no treatment | # of mice at start/ # mice reaching 10x |
|---|---|---|---|---|---|
| No treatment | | 19.5 | 1.6 | -- | 10/10 |
| IDD-P vehicle i.v. | 5/2/5 | 20.6 | 1.3 | n.s | 9/9 |
| 9NC in IDDP 2.5 mg/kg i.v. | 5/2/5 | 34.3 | 2.0 | <<0.05 | 10/10 |
| 9NC in IDDP 1.75 mg/kg i.v. | 5/2/5 | 25.7 | 1.3 | <0.01 | 10/10 |
| 9NC in IDDP 1.25 mg/kg i.v. | 5/2/5 | 24.6 | 1.0 | =.01 | 10/10. |
| Camptosar 100 mg/kg i.p.. | QWK x 3 | 30.5 | 3.9 | <0.05 | 10/10 |
| Hycamtin 10 mg/kg i.p. | Q4D x 4 | 30.6 | 1.5 | <<0.05 | 10/10 |

FIGURE 15

HT-29 Human Colon Cancer Xenograft Study

| Treatment | Schedule | Mean Days to 10 X | S.E.M | P vs. no treatment | # of mice at start/ # mice reaching 10x |
|---|---|---|---|---|---|
| No treatment | | 26.9 | 2.0 | -- | 8/8 |
| IDD-P vehicle i.v. | 5/2/5 | 29.4 | 1.6 | n.s | 8/8 |
| 9NC in IDDP 2.5 mg/kg i.v. | 5/2/5 | 34.0 | 1.8 | <0.05 | 8/8 |
| 9NC in IDDP 1.75 mg/kg i.v. | 5/2/5 | 34.5 | 2.0 | <0.05 | 9/9 |
| 9NC in IDDP 1.25 mg/kg i.v. | 5/2/5 | 38.1 | 3.6 | <0.05 | 9/9. |
| Camptosar 100 mg/kg i.p.. | QWK x 3 | 35.7 | 2.2 | <0.01 | 9/9 |
| Hycamtin 10 mg/kg i.p. | Q4D x 4 | 34.4 | 1.5 | <0.01 | 9/9 |

FIGURE 16

SKMES Human Lung Cancer Xenograft Study

| Treatment | Schedule | Mean Days to 10 X | S.E.M | P vs. no treatment | # of mice at start/ # mice reaching 10x |
|---|---|---|---|---|---|
| No treatment | | 11.7 | 0.8 | -- | 10/10 |
| IDD-P vehicle i.v. | 5/2/5 | 14.6 | 1.0 | 0.03 | 10/10 |
| 9NC in IDDP 2.5 mg/kg i.v. | 5/2/5 | 27.3 | 1.6 | <<0.05 | 10/10 |
| 9NC in IDDP 1.75 mg/kg i.v. | 5/2/5 | 29.4 | 2.2 | <<0.05 | 10/10 |
| 9NC in IDDP 1.25 mg/kg i.v. | 5/2/5 | 35.2 | 5.7 | <0.05 | 10/10. |
| Camptosar 100 mg/kg i.p.. | QWK x 3 | 35.2 | 4.4 | <<0.05 | 10/10 |
| Hycamtin 10 mg/kg i.p. | Q4D x 4 | 33.6 | 3.6 | <<0.05 | 10/10 |

INJECTABLE PHARMACEUTICAL COMPOSITION COMPRISING COATED PARTICLES OF CAMPTOTHECIN

BACKGROUND OF THE INVENTION

1. Field of the Invention

This invention relates to compositions and methods for delivering camptothecin, in particular, 9-nitro-camptothecin, to patients by injection and treating diseases associated with abnormal cell proliferation such as cancer.

2. Description of Related Art

Camptothecin was isolated from the plant, *Camptotheca acuminata*, in the 1960's (Wall, M. et al. (1966) J. Am. Chem. Soc. 88: 3888–3890). Camptothecin has a pentacyclic ring system with only one asymmetric center in ring E with a 20(S)-configuration. The pentacyclic ring system includes a pyrrole quinoline moiety (rings A, B and C), a conjugated pyridone (ring D), and a six-membered lactone (ring E) with an α-hydroxyl group (i.e., an α-hydroxy lactone).

Camptothecin itself is highly lipophilic and poorly water-soluble. Sodium camptothecin that is solubilized by sodium hydroxide in water was used in clinical trials in the early 70's and found to have antitumor activity. However, this formulation of camptothecin administered via i.v. caused unpredictable side effects such as myelosuppression and hemorrhagic cystitis. Clinical trials with sodium camptothecin were eventually discontinued because of these toxicities and the lack of consistent antitumor activity.

Continued evaluation of this agent showed that the sodium carboxylate salt is only 10% as potent as the native camptothecin with the closed α-hydroxy lactone ring intact (Wall et al. in (1969) "International Symposium on Biochemistry and Physiology of the Alkaloids, Mothes et al. eds. Academic Verlag, Berlin, 77; Giovanella et al. (1991) Cancer Res. 51:3052). Studies also showed that camptothecin and its derivatives undergo an alkaline hydrolysis of the E-ring α-hydroxy lactone, resulting in a carboxylate form of camptothecin. At pH levels below 7.0, the α-hydroxy lactone E-ring form of camptothecin predominates. However, intact lactone ring E and α-hydroxyl group have been shown to be essential for antitumor activity of camptothecin and its derivatives.

Camptothecin and its derivatives have been shown to inhibit DNA topoisomerase I by stabilizing the covalent complex ("cleavable complex") of enzyme and strand-cleaved DNA. Inhibition of topoisomerase I by camptothecin induces protein-associated DNA single-strandbreaks which occur during the S-phase of the cell cycle. Since the S-phase is relatively short compared to other phases of the cell cycle, longer exposure to camptothecin should result in increased cytotoxicity of tumor cells. Studies indicate that only the closed α-hydroxy lactone form of the drug helps stabilize the cleavable complex, leading to inhibition of the cell cycle and apoptosis.

To preserve the α-hydroxy lactone form of camptothecin, camptothecin and its water insoluble derivatives have been dissolved in N-methyl-2-pyrrolidinone in the presence of an acid (U.S. Pat. No. 5,859,023). Upon dilution with an acceptable parenteral vehicle, a stable solution of camptothecin was obtained. The concentrated solution of camptothecin was also filled in gel capsules for oral administration. It is believed that such formulations increase the amount of lipophilic α-hydroxy lactone form of camptothecin that diffuse through the cellular and nuclear membranes in tumor cells.

T. G. Burke, A. E. Staubus, A. K. Mishra and H. Malak ("Liposomal Stabilization of Camptothecin's Lactone Ring." J. Am. Chem. Soc. 1992, 114, 8318) and T. G. Burke, A. K. Mishra, M. C. Wani and M. E. Wall ("Lipid bilayer partitioning and stability of camptothecin drugs." Biochemistry May 25, 1993 ; 32 (20):5352–64) have demonstrated that harboring of camptothecin drugs into phospholipid bilayer membranes stabilized the α-hydroxy lactone moiety of camptothecin drugs against hydrolysis. In comparison to hydrolysis half-lives in PBS at 37° C. of approximately 15 to 30 min, lipid bilayer membrane-bound camptothecin drugs were found to be stable even for periods up to 72 hours. These authors have determined an iodide ion induced quenching behavior of camptothecin's fluorescence indicative of intercalation of camptothecin molecules between the phospholipid acyl chains of membrane bilayers, a protected environment removed from the aqueous interface. The potential for stabilization of camptothecin's α-hydroxy lactone ring structure in this environment led to the expectation that lipid bilayer intercalation might conserve the biologically active form in vivo, thereby permitting the active form to be delivered via liposomal bilayers into a biological host (U.S. Pat. No. 5,552,156).

Z Mi and T. G. Burke ("Differential interactions of camptothecin lactone and carboxylate forms with human blood components." Biochemistry Aug. 30, 1994; 33 (34): 10325–36) exploited the intrinsic fluorescent emissions from the α-hydroxy lactone and carboxylate forms of camptothecin in order to elucidate their markedly different interactions with the various components of human blood. It was found that in PBS at pH 7.4, human serum albumin (HSA) preferentially binds the carboxylate form of camptothecin with a 150-fold higher affinity than the α-hydroxy lactone form. These interactions cause camptothecin's α-hydroxy lactone ring to open more rapidly and completely in the presence of HSA than in the protein's absence. In human plasma, at pH 7.4 and 37° C., they have observed camptothecin's α-hydroxy lactone ring to open rapidly and fully to the carboxylate form (half-life=11 min; % α-hydroxy lactone at equilibrium, 0.2%). They concluded that camptothecin carboxylate's fluorophore locates in a hydrophobic binding pocket in native HSA. In whole blood versus plasma, camptothecin's α-hydroxy lactone was found to display enhanced stability resulting in an increased half-life of 22 min and an equilibrium α-hydroxy lactone concentration of 5.3%. The enhanced stability of camptothecin in human blood was found to be due to drug associations with the lipid bilayers of red blood cells. Although camptothecin α-hydroxy lactone hydrolysis slows down and the equilibrium α-hydroxy lactone form concentration rises on intercalation within phospholipid bilayers, the membrane-bound drug still remains thermodynamically and kinetically too labile in the presence of albumin and the concentration of the active (α-hydroxy lactone form in plasma remains insufficient. Thus, the liposomal bilayers cannot be considered as a pragmatic delivery system for this drug. It is speculated that a principal deactivation channel of membrane bilayer-bound camptothecin is facilitated via high affinity of the carboxylate form of the drug with albumin in-vivo compared to a relatively lower affinity of the α-hydroxy lactone form of the drug with the membrane bilayers.

U.S. Pat. Nos. 5,552,156 and 5,736,156 describe liposomes and micelles of surfactant molecules for intravenous delivery of camptothecins. In liposomes, the camptothecin can reside bound to and partially in the membrane interlayer or dissociate into the internal enclosed aqueous layer in direct contact with water where the camptothecin lactone is not stable to hydrolysis. In micelles of surfactant molecules, the camptothecin is either in the central hydrocarbon portion of the micelle, bound to the micelle membrane or bound to the outside of the micelle. However, while camptothecins are less stable in micelles than in liposomes, especially in poly(ethylene oxide)-containing micelles, the amount of camptothecin compound that can bind to the membrane layer in a liposome is limited to the dimensions of the membrane and to the requirement that the membrane remain intact to prevent rupture of the liposome. The ratio of lipid to camptothecin in liposomes is generally greater than 150, and the lactone of the camptothecin slowly hydrolyzes because of the reported equilibrium between bound and free camptothecin.

SUMMARY OF THE INVENTION

The present invention provides novel injectable formulations of camptothecin, including analogs, derivatives, and pharmaceutically active metabolites of 20(S)-camptothecin, referred to herein as camptothecin compound. The present invention also provides methods of manufacturing these formulations, kits containing these formulations and methods of using these formulations to treat patients having diseases associated with abnormal cell proliferation, such as cancer.

One class of injectable formulations comprise micron and submicron size particle suspensions of a camptothecin. These micron and submicron size particle suspensions of camptothecin substantially reduce deactivation of the camptothecin by hydrolysis in-vitro and by plasma components in-vivo. The particle suspensions of the present invention display efficacy in the treatment of diseases associated with abnormal cell proliferation such as cancer when injected intravenously into mammals containing such diseases. The micron and submicron size particle suspensions of α-hydroxy lactone-containing camptothecin drugs of this invention are preferably substantially stable to autoclaving, undergoing sterilization without suffering from hydrolytic deactivation of the α-hydroxy lactone or substantial change in particle size. The particle suspensions can be autoclaved, cooled, and stored for long periods without undergoing agglomeration, flocculation, or aggregation.

In one embodiment, the injectable formulation comprises an aqueous suspension of solid particles suitable for intravenous delivery, the solid particles comprising a camptothecin, the solid particles having mean diameters between about 0.05 $\mu$m and 10 $\mu$m, the particles coated with a 0.3 nm to 3.0 $\mu$m thick layer of a membrane-forming amphipathic lipid.

In another embodiment, the injectable pharmaceutical composition comprises an aqueous suspension of solid particles suitable for intravenous delivery, the solid particles comprising a camptothecin, and a 0.3 nm to 3.0 $\mu$m thick outer layer comprising a membrane-forming amphipathic lipid; wherein the solid particles have mean diameters between about 0.05 $\mu$m and 10 $\mu$m.

In yet another embodiment, an injectable pharmaceutical composition is provided which comprises: a dispersion of micrometer to submicrometer size solid particles in an aqueous carrier solution comprising one or more pharmaceutically acceptable tonicity modifier agents, the solid particles comprising a camptothecin, a first coating of not more than 10% w/w of a substantially water-insoluble, pharmaceutically acceptable lipophilic agent in which the camptothecin drug is insoluble or poorly soluble, and a second coating of at least one membrane-forming surface stabilizing amphipathic lipid, wherein the dispersion does not aggregate, flocculate, or agglomerate, and the particles do not grow in size above a volume weighted mean diameter of 10 $\mu$m upon thermal sterilization.

In yet another embodiment, an injectable pharmaceutical composition is provided which comprises: a dispersion of micrometer to submicrometer size solid particles in an aqueous carrier solution comprising one or more pharmaceutically acceptable tonicity modifier agents, the solid particles comprising: a camptothecin, and a coating of at least one membrane-forming surface stabilizing amphipathic lipid, wherein the dispersion does not aggregate, flocculate, or agglomerate, and the particles do not grow in size above a volume weighted mean diameter of 10 $\mu$m upon thermal sterilization.

In yet another embodiment, a pharmaceutical composition suitable for intravenous administration to a mammal is provided which comprises: an aqueous suspension of particles having mean diameters between about 0.05 $\mu$m and 10 $\mu$m, the particles comprising a camptothecin having an intact lactone ring, a membrane-forming amphiphatic lipid coating an outer surface of the particle, and one or more tonicity modifying agents, wherein the ratio of lipid to camptothecin in the particle is less than about 150:1 moles:mole, and wherein the mean diameters of the particles increase less than 100% upon thermal sterilization.

Another class of injectable formulations comprise an aqueous dispersion of microdroplets suitable for intravenous delivery, the microdroplets comprising a camptothecin. It is noted with regard to the microdroplet formulations that the camptothecin may be present where it is dissolved in a water-insoluble, pharmacologically acceptable liquid. The camptothecin may also be present in a solid form in addition to being dissolved in the water-insoluble, pharmacologically acceptable liquid. For example, the camptothecin may be present in the water-insoluble, pharmacologically acceptable liquid beyond the solubility of the camptothecin in the liquid.

In one embodiment, the injectable pharmaceutical composition comprises: an aqueous suspension of microdroplets suitable for intravenous delivery, the microdroplets having a mean diameter between 200 Angstroms and one micron, the microdroplets comprising a substantially water-insoluble, pharmacologically acceptable liquid, a camptothecin dissolved in the water-insoluble, pharmacologically acceptable liquid, and an outer layer comprising a phospholipid.

In another embodiment, the injectable pharmaceutical composition comprises: a dispersion in an aqueous carrier solution comprising one or more pharmaceutically acceptable tonicity modifier agents and liquid droplets of micrometer to submicrometer, the droplets comprising a substantially water-insoluble, pharmaceutically acceptable lipophilic liquid vehicle a camptothecin dissolved in the lipophilic liquid vehicle, and an outer layer surrounding the droplet comprising at least one membrane-forming amphipathic lipid, wherein upon thermal sterilization the dispersion does not aggregate, flocculate, agglomerate, or coalesce, and the droplets do not grow in size above a volume weighted mean diameter of 10 $\mu$m.

In yet another embodiment, the injectable pharmaceutical composition comprises: an aqueous carrier solution comprising one or more pharmaceutically acceptable tonicity modifier agents; a dispersion of liquid droplets of a first size distribution, the liquid droplets comprising a substantially water-insoluble, pharmaceutically acceptable lipophilic liquid vehicle, solid particles of a camptothecin of a second size distribution, and an outer layer surrounding the droplet comprising at least one membrane-forming amphipathic lipid; wherein the first size distribution is in the range of submicrometer to micrometers, and the second size distribution is smaller than the first size distribution; and wherein upon thermal sterilization, the dispersion does not aggregate, flocculate, agglomerate, or coalesce, and the droplets do not grow in size above a volume weighted mean diameter of 10 µm.

The camptothecins used in the formulations of the present invention may be an analog, a derivative or a pharmacologically active metabolite of 20(S)-camptothecin. In one embodiment, the camptothecin compound in the formulation has poor water solubility, for example having a water solubility of 10 µg/ml or less.

Examples of the camptothecins include, but are not limited to, 20(S)-camptothecin, 9-nitro-20(S)-camptothecin, 9-amino-20(S)-camptothecin, 7-ethyl-10-(4-(1-piperdino)-1-piperdino)-carbonyloxy-camptothecin, 7-ethyl-10-hydroxy-20(S)-camptothecin, 10,11-methylenedioxy-20(S)-camptothecin 9-chloro-20(S)-camptothecin, 9-bromo-20(S)-camptothecin, 9-hydroxy-20(S)-camptothecin, and 11-hydroxy-20(S)-camptothecin.

With regard to each of the formulations described herein, the camptothecin compound preferably contains a α-hydroxy lactone ring and is most preferably 9-nitro-20(S)-camptothecin.

According to these various embodiments, the pharmaceutical composition preferably has a pH less than 7, preferably a pH less than 6 and in one embodiment, a pH between 5 and 6.

Also according to these various embodiments, the membrane-forming amphipathic lipid optionally comprises a phospholipid. The phospholipid may optionally be selected from the group consisting of saturated phospholipids, unsaturated phospholipids, synthetic phospholipids, natural phospholipids, and combinations thereof. The phospholipid may optionally be selected from the group consisting of natural and synthetic lipids, hen egg-derived phospholipid, egg phospholipid, purified egg phospholipid, soy phospholipid, dimyristoyl lecithin, didodecanoyl lecithin, dioeoyl lecithin, dilinoeoyl lecithin, alpha-palmito-beta-oleoyl lecithin, alpha-palmitoyl-beta-linoleoyl lecithin, alpha-oleoyl-beta-palmitoyl lecithin, diarachidonyl lecithin, alpha-palmito-beta-myristoyl lecithin, dimyristoyl phosphatidic acid, dipalmitoyl phosphatidic acid, distearoyl phosphatidic acid, phosphatidyl serine, phosphatidyl inositol, dimyristoyl phosphatidyl glycerol, dipalmitoyl phosphatidyl glycerol, dioctadecanoyl phosphatidyl ethanolamine, dioleoyl phosphatidyl ethanolamine, dihexadecyl phosphatidyl ethanolamine, dilauryl phosphatidyl ethanolamine, dimyristoyl phosphatidyl ethanolamine, dipalmitoyl phosphatidyl ethanolamine, Lipoid E80, Lipoid ES, Lipoid 90H, and Lipoid 100H. In one particular variation, the phospholipid comprises Lipoid E80.

Also according to these various embodiments, the outer layer may further comprises cholesterol.

Also according to these various embodiments, the camptothecin may be present in amounts of up to about 25% w/w, more preferably up to about 5% w/w. The camptothecin may be present in amounts of from about 0.05% w/w to about 5% w/w, and optionally from about 0.1% w/w to about 1% w/w. In one particular variation, the camptothecin is present in amount of about 0.2% w/w.

Also according to these various embodiments, the membrane-forming amphipathic lipid may be present in amounts of from 0.2% w/w to about 5% w/w, more preferably in amounts of from 1% w/w to about 5% w/w. In one particular variation, the membrane-forming amphipathic lipid is present in amounts of about 4% w/w.

According to each of the above embodiments, the mean diameters of the particles and droplets preferably increase less than 100% upon storage at room temperature (23° C.) for at least 1 month, more preferably at least 3 months, more at least 6 months, and most preferably at least 1 year.

Also according to each of the above embodiments, the lipophilic liquid vehicle is optionally present in amounts up to about 40% w/w, more preferably in amounts up to about 25% w/w, and most preferably in amounts up to about 20% w/w. The lipophilic liquid vehicle is also preferably present in amounts greater than 0.5% w/w.

The various compositions and kits of the present invention may be used in methods to treat patients suffering from abnormal cell proliferation such as cancer including hematological malignancy and tumors. In one embodiment, the method comprises: providing a pharmaceutical composition according to the present invention; and administering a therapeutically effective amount of the pharmaceutical composition intravenously to a patient in need thereof. According to the method, the camptothecin compound preferably contains a α-hydroxy lactone ring and is preferably 9-nitro-20(S)-camptothecin.

BRIEF DESCRIPTION OF THE DRAWINGS

FIG. 1 describes IDD-P or IDD-D formulations which are used in the human cancer studies described herein.

FIG. 2 summarizes the volume weighted mean particle size and 99.9 percentile data for the temperature stability study for IDD-P.

FIG. 3 summarizes the particle size stability data from stability studies on IDD-D.

FIG. 4 summarizes the protocol design for the first 375 melanoma study.

FIG. 5 summarizes the therapeutic and toxic responses for all mice groups in the first 375 melanoma study.

FIG. 11 provides a time to ten-fold growth in tumor size analysis for data from the second melanoma study.

FIGS. 12A—12D provide individual mouse data for the second 375 melanoma study.

FIG. 12A provides individual mouse data for the first group from the second 375 melanoma study.

FIG. 12B provides individual mouse data for the second group from the second 375 melanoma study.

FIG. 12C provides individual mouse data for the third group from the second 375 melanoma study.

FIG. 12D provides individual mouse data for the fifth group from the second 375 melanoma study.

FIG. 13 illustrates the protocol design and study results evaluating IDD-P in a MX-1 human breast cancer xenograft study.

FIG. 14 illustrates the protocol design and study results evaluating IDD-P in a pan c-human pancreatic cancer xenograft study.

FIG. 15 illustrates the protocol design and study results evaluating IDD-P in a HT-29 human colon cancer xenograft study.

FIG. 16 illustrates the protocol design and study results evaluating IDD-P in a SKMES human lung cancer xenograft study.

DETAILED DESCRIPTION OF THE INVENTION

Figure 6:
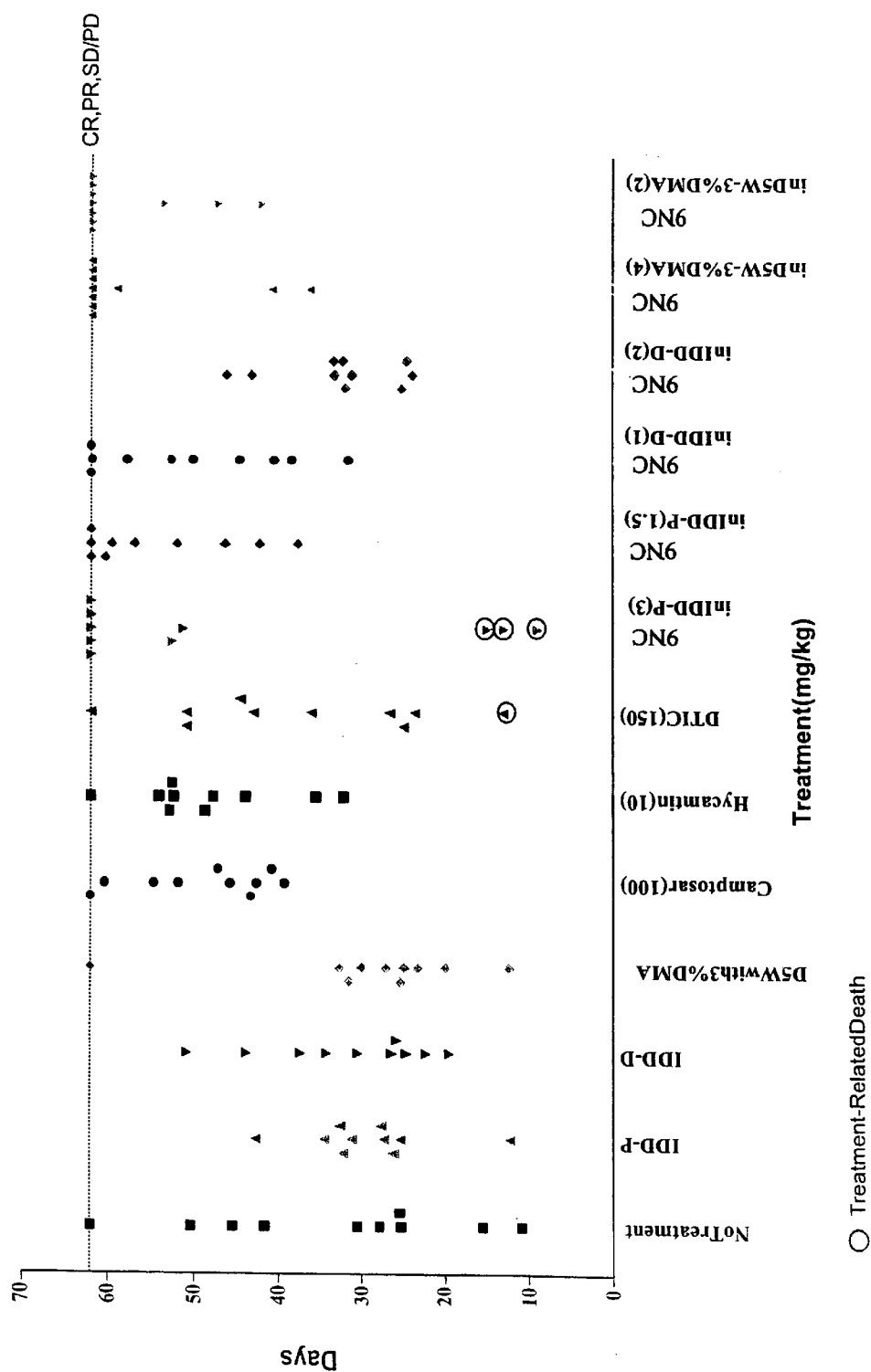
FIG. 6 illustrates a scatter plot showing the individual survival times for the mice in all groups in the first 375 melanoma.

The present invention provides novel compositions that comprise camptothecin compounds that include analogs, derivatives and pharmacologically active metabolites of 20(S)-camptothecin (collectively referred to herein as "camptothecin compounds") for the treatment of neoplastic diseases or diseases associated with abnormal cell proliferation. The present invention also provides methods for treating these diseases through the delivery of the camptothecin compound comprising compositions of the present invention. The compositions are designed to be injectable and are preferably delivered intraveneously or intrathecally.

One feature of the present invention is that the camptothecin compound, especially a water-insoluble one such as 9-nitro-camptothecin, is solubilized and stabilized in an injectable formulation comprising an aqueous suspension of solid particles comprising the camptothecin, the solid particles having mean diameters between about 0.05 $\mu$m and 10 $\mu$m, the particles coated with a 0.3 nm to 3.0 $\mu$m thick layer of a membrane-forming amphipathic lipid. Alternatively, the camptothecin compound, especially a water-insoluble one such as 9-nitro-camptothecin, is solubilized and stabilized in microdroplets having a mean diameter less than one micron, and optionally between 200 Angstroms and one micron, the droplets comprising a substantially water-insoluble, pharmacologically acceptable liquid containing a camptothecin surrounded by a layer comprising a phospholipid.

Another feature of the present invention is that the camptothecin compound, especially a water-insoluble one such as 9-nitro-camptothecin, is stabile to steam sterilization in the injectable formulations of the present invention. In one embodiment, an aqueous dispersion of solid particles is provided which comprises a camptothecin as solid particles having mean diameters between about 0.05 $\mu$m and 10 $\mu$m wherein the solid particles are surface stabilized with at least one membrane-forming amphipathic lipid, preferably a phospholipid, and wherein the solid particles are dispersed in a continuous phase of a carrier, the carrier being an aqueous solution of one or more pharmaceutically acceptable tonicity modifier agents. Alternatively, the camptothecin compound is solubilized and stabilized as a thermally sterilized (or sterilizable) injectable aqueous dispersion of microdroplets having a mean diameter less than 2 $\mu$m, and optionally between 200 Angstroms and 1 $\mu$m, the microdroplets comprising a substantially water-insoluble, pharmaceutically acceptable lipophillic liquid containing the camptothecin compound and at least one membrane-forming amphipathic lipid, preferably a phospholipid, wherein the microdroplets are surrounded by a layer comprising the membrane-forming amphipathic lipid, and wherein the microdroplets are dispersed in a continuous phase of an aqueous carrier solution of one or more pharmaceutically acceptable tonicity modifier agents.

The inventors have discovered that significant tumor growth suppression activity of camptothecins, particularly 9-nitro-camptothecin, can be achieved when the formulations according to the present invention are administered by injection, particularly by an intravenous route. Further, tumor growth suppression activity has been shown for multiple different types of cancers, including melanoma, breast cancer, liver cancer and pancreatic cancer.

1. Camptothecin Compounds

"Camptothecin compound", as it is referred to in the present invention, includes the plant alkaloid 20(S)-camptothecin, water insoluble or substantially water insoluble analogs, derivatives, prodrugs and pharmaceutically active metabolites of 20(S)-camptothecin. Examples of camptothecin derivatives include, but are not limited to, 9-nitro-20(S)-camptothecin, 9-amino-20(S)-camptothecin, 9-methyl-camptothecin, 9-chloro-camptothecin, 9-flouro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin. Prodrugs of camptothecin include, but are not limited to, esterified camptothecin derivatives as described in U.S. Pat. No. 5,731,316, such as camptothecin 20-O-propionate, camptothecin 20-O-butyrate, camptothecin 20-O-valerate, camptothecin 20-O-heptanoate, camptothecin 20-O-nonanoate, camptothecin 20-O-crotonate, camptothecin 20-O-2',3'-epoxy-butyrate, nitro-camptothecin 20-O-acetate, nitro-camptothecin 20-O-propionate, and nitro-camptothecin 20-O-butyrate.

In an embodiment, the camptothecin compound has poor water solubility, for example, 10 $\mu$g/ml or less. Examples of camptothecin compounds with poor water solubility include, but are not limited to, 9-nitro-20(S)-camptothecin, 9-amino-20(S)-camptothecin, 7-ethyl-10-(4-(1-piperdino)-1-piperdino)-carbonyloxy-camptothecin, 7-ethyl-10-hydroxy-20(S)-camptothecin, 10,11-methylenedioxy-20(S)-camptothecin, 9-chloro-20(S)-camptothecin, 9-bromo-20(S)-camptothecin, 9-hydroxy-20(S)-camptothecin, and 11-hydroxy-20(S)-camptothecin. In a preferred embodiment, the modified 20(S)-camptothecin is 9-nitro-20(S)-camptothecin.

Native, unsubstituted, the plant alkaloid camptothecin can be obtained by purification of the natural extract, or may be obtained from the Stehlin Foundation for Cancer Research (Houston, Tex.). Substituted camptothecins can be obtained using methods known in the literature, or can be obtained from commercial suppliers. For example, 9-nitro-camptothecin may be obtained from SuperGen, Inc. (San Ramon, Calif.), and 9-amino-camptothecin may be obtained from Idec Pharmaceuticals (San Diego, Calif.). Camptothecin and various of its analogs and derivatives may also be obtained from standard fine chemical supply houses, such as Sigma Chemicals.

2. Injectable Compositions of the Present Invention

The present invention relates to pharmaceutical compositions suitable for use in delivering a camptothecin by injection. The pharmaceutical compositions may be divided into two categories: (a) phospholipid stabilized particulate aqueous dispersion of a camptothecin that is stable to sterilization, especially by autoclaving; and (b) phospholipid stabilized aqueous dispersion of microdroplet containing a camptothecin that is stable to sterilization, especially by autoclaving. Each composition type is described herein.

Pharmaceutical compositions according to the invention may additionally contain suitable amounts of pH buffering salts and pH adjusting agents such as sodium hydroxide and/or pharmaceutically acceptable acids. Phospholipids molecules can undergo hydrolysis at pH lower than 5 and higher than 9. Therefore, the pH of the aqueous carrier medium for the particulate or droplet dispersion is preferably adjusted to within this range prior to homogenization, and if necessary readjusted prior to sterilization particularly when autoclaving by steam is used.

It is further noted with regard to the formulations of the present invention that the formulations are preferably acidic, i.e., have a pH less than 7 in order to stabilize the $\alpha$-hydroxy lactone ring of camptothecins. In a more preferred embodiment, the formulations have a pH less than 6.5, more preferably less than 6. Optionally, the pH of the formulations are between 5 and 7, more preferably between 5 and 6.5 and most preferably between 5 and 6.

All parts and percentages reported herein are by weight (w/w) or weight/volume (w/v) percentage, in which the weight or volume in the denominator represents the total weight or volume of the system. Concentrations of water soluble constituents in aqueous solution (e.g. glucose) are given in millimolar concentration (mM=millimoles per liter) referred to the volume of water in the system. All temperatures are reported in degrees Celsius. Diameters or dimensions are given in millimeters (mm=$10^{-3}$ meters), micrometers ($\mu$m,=$10^{-6}$ meters), nanometers (nm=$10^{-9}$ meters) or Angstrom units (=0.1 nm). The compositions of the invention can comprise, consist of, or consist essentially of the materials set forth and the process or method can comprise, consist of, or consist essentially of the steps set forth with such materials.

A. Surface Stabilized Solid Particulate Dispersion of a Camptothecin of Micrometer to Submicrometer Dimensions According to one pharmaceutical composition category according to the present invention, the composition comprises a phospholipid stabilized particle dispersion of a camptothecin, preferably 9-nitro-camptothecin. Procedures for making this category of pharmaceutical composition, as well as varying embodiments, are described in U.S. Pat. Nos. 5,091,187, 5,091,188, Re 35,338, 5,145,684 and 5,494,683, which are each incorporated by reference.

In one embodiment according to this category, the pharmaceutical composition comprises an aqueous suspension of solid particles comprising a camptothecin, the solid particles having mean diameters between about 0.05 $\mu$m and 10 $\mu$m, the particles coated with a 0.3 nm to 3.0 $\mu$m thick layer of a membrane-forming amphipathic lipid.

In another embodiment according to this category, the pharmaceutical composition of a camptothecin comprises an injectable aqueous dispersion of micrometer to submicrometer size solid particles suitable for intravenous delivery, the dispersed solid particles comprising a camptothecin, surface stabilized with at least one membrane-forming amphipathic lipid, preferably a phospholipid and the solid particle phase dispersed in a continuous phase of a carrier aqueous solution of pharmaceutically acceptable tonicity modifier agents. The dispersed solid particles are preferably stable to steam sterilization, also referred to herein as autoclaving.

The size of the dispersed camptothecin particles may be controlled using low shear which produces relatively larger particles and high shear which produces relatively smaller particles. Low shear methods include Waring Blender, "high" and propeller homogenization and rotating tube and plunger homogenizers. High shear methods include the French Pressure Cell or "French Press" (SLM Instruments, Urbana, Ill.), sonication (Heat Systems Co., Melville, N.Y.) and Microfluidization (Microfluidics Corp., Newton Mass.). The latter, which is described by Mayhew et al. in Biochim. Biophys Acta 775:169–174, 1984, is particularly well suited for commercial production. In addition, other high energy processes providing the forces of attrition, impaction, high shear, antisolvent and solvent precipitation, rapid expansion of a compressed normal or supercritical solution and the like in the presence of a membrane-forming amphipathic lipid can be used to produce these stable sub-micrometer and micrometer size particle dispersions.

In a preferred embodiment, the camptothecin forms a solid core of the particle, and the solid core is stabilized by the membrane forming phospholipid. Alternatively, camptothecin molecules entrapped within or below lipid membrane bilayers or monolayers can form a coating over another pharmaceutically-acceptable solid material comprising the core of the particle which is stabilized by the membrane forming phospholipid. In either case the core material should be reduced to <10 $\mu$m or submicron dimensions and dispersed in an aqueous medium as a particle stabilized by a membrane forming phospholipid.

Particle size reduction can be accomplished by sonication or other high energy treatments involving high shear or forces of attrition or impaction in the presence of a membrane forming lipid, preferably one or a combination of more than one phospholipids. Phospholipids (or other membrane forming lipids) present during the high energy particle size reduction step envelope the freshly generated micrometer to submicrometer size core material to stabilize the particle. Thus, a requirement for this process is that the phospholipids (or other membrane forming lipids) and the core material be present together during the sonication or other high-energy particle size reduction and dispersion process. The common aspect or all of these preparative methods is that the molecules of the phospholipid (or other membrane forming lipids) must have direct access to the core material during the particle size reduction process to form a primary coating on the core.

It is possible to increase the relative thickness or amount of the membrane forming material associated with the primary coating by adding additional phospholipid to the suspension after sonication or other application of high shear for example by suspending the added phospholipid by homogenization at low shear (for example, using "high speed homogenizers", propeller homogenizers, Waring blender, or rotating tube and plunger homogenizers).

The resulting particle should be steam sterilizable such that the size of the particle does not substantially change as a result of being sterilized. The size of the particle should also be stable over time and to changes in temperature.

In addition to making use of phospholipids and other membrane-forming lipids as a particle enveloping and surface stabilizing material, the present invention utilizes the membrane-forming lipids as mechanical buffers, organizers of aqueous volume and retardants of recrystallization of the drug. This is achieved by excess phospholipid (or other membrane forming lipids) in the form of unilamellar and multi-lamellar vesicles. Unilamellar vesicles of the phospholipid (or other membrane forming lipids) are formed as the main byproduct of the high energy particle size reduction step. Their retention in the preparation was found to improve the long-term stability of the formulation. Also, preformed multi-lamellar vesicles (made by homogenization) or unilamellar vesicles can be added to the preparation to improve its stability or pharmacokinetics. The vesicles of the phospholipid (or other membrane forming lipids) may remain loosely attached to the micrometer to submicrometer size dispersed particle. These peripheral vesicles associate and dissociate continuously in the preparation. Previous experimentation, described in U.S. Pat. No. 5,091,188, has shown that these loosely attached vesicles can be removed by repeated centrifugation and resuspension of the preparation.

When a peripheral phospholipid is present at 20% (w/v), the majority of the aqueous volume of the preparation is enclosed within phospholipid membranes. This serves as a topological barrier to recrystallization of the drug. Reformed crystals can not be larger than the diameter of the vesicles or distance between the vesicles.

In another aspect, when the camptothecin is entrapped between the membrane layers, it is necessary to provide another material to comprise the particle core material of the particle. This can be any pharmaceutically-acceptable water-insoluble substance which should generally have a water solubility of <5 mg/ml at physiological pH (6.5–7.4). It can be selected from, but is not limited to, paraffin, tristearin, ethyl oleate, cetostearyl alcohol, cetyl alcohol, myristyl alcohol, stearyl alcohol, petrolatum or biocompatible polymer. The core material can also be another pharmaceutically active agent. There are many cases in which combination therapy with camptothecin is desirable.

Sonication or a high-energy particle size reduction step is most conveniently carried out with the core material at concentrations of 25% (w/v) or less and the membrane-forming lipid at 0.5% or greater. It is also convenient to add further core material and to repeat the process. With a single batch method or step-wise addition, final concentrations of up to 30% core material can be achieved. The sonication or other high-energy particle size reduction process results in a syringable aqueous dispersion of surface stabilized particles of predominantly sub-micrometer dimensions, with the particles exhibiting Brownian motion. In some cases, over a period of 1–2 days to several weeks, the dispersions can settle creating a distinct sedimented zone in which the concentration of core material is 20–60% (w/v). The final concentration and volume are dependent on the choice of core material and upon the choice of the concentration of phospholipid (or other membrane forming lipids) in the loosely attached peripheral domain.

In most preparations the sedimented material is resuspendable with inversion or gentle agitation to give a homogeneous and syringable suspension, even after a period of months. In preferred compositions of this invention, any sedimented material is resuspendable with inversion or gentle agitation to give a homogeneous and syringable suspension, even after a period of months.

The slow sedimentation process can be used to concentrate the preparation. Removal of the volume above the sedimentation zone after 1–2 days results in preparations in which the core material is at 20–60% (w/v). Long-term storage typically results in no further settling. The preparations remain homogeneous, syringable and pharmaceutically acceptable for many months. Microscopic examination of these preparations reveals distinct micron and sub-micron diameter particles of core material. The volume between these is almost completely filled with the primary enveloping layers and by phospholipid vesicles. The particles exhibit only restricted Brownian Motion. Under microscopic observation they are not observed to change position in relation to each other. They vibrate or "dance in place" about their central position. This partial restriction of motion is probably an important factor in the long-term stability of the preparation.

Sterilized aqueous dispersions of camptothecin according to the present invention can be put into dry form by lyophilization to yield a powder which can be later reconstituted with a pharmaceutically acceptable fluid prior to use.

In a preferred embodiment, a preferred composition can be obtained according to this invention by first forming a solution by dissolving the water soluble components such as pH buffering agents and tonicity modifiers such as mannitol and/or trehalose in a required quantity of water. Mannitol or trehalose are known to modify osmotic pressure to provide osmolalities of the suspensions suitable for intravenous injection. A suitable osmolality for an injectable formulation of this invention is one for example that is substantially isotonic with blood. Preferably, a pharmaceutically acceptable pH buffering agent is used. A particularly preferred pH buffering agent is sodium acetate/acetic acid.

A pre-mix dispersion may be prepared under a nitrogen atmosphere by adding a required quantity of one or more membrane-forming amphipathic lipids, preferably one or more phospholipids such as Lipoid E80, and a solid powder of 9-nitro-camptothecin to the aqueous solution while mixing under high shear to mix the powder and the membrane-forming lipid in the presence of the carrier solution. The pH of the premix is adjusted with 1N NaOH or 20% acetic acid to about 5.5. The acidification of the premix helps to reduce potential hydrolysis of the $\alpha$-hydroxy lactone ring of 9-nitro-camptothecin during this part of the preparation.

The pre-mix dispersion is then subjected to high pressure homogenization with cooling as needed, preferably under nitrogen and preferably at pressures in the range of 10,000 psi to 25,000 psi for a number of volume passes sufficient to achieve a desired particle size distribution. The homogenized suspension is then treated with one or more tonicity modifiers such as mannitol or trehalose and water, buffered to about 5.5, filled into vials, stoppered under a nitrogen atmosphere, and autoclaved preferably using terminal steam sterilization for example above 100° C. at about 121° C. or hotter for about 15 to 30 minutes or longer and then cooled.

The volume-weighted diameters and the particle size distribution of the resulting steam sterilized suspensions may be determined with a Malvern Mastersizer Microplus apparatus which utilizes a method based on diffraction of light by the particulate suspension to provide a measure of particle size.

These suspensions can be further diluted for example with water for injection or other suitable sterile aqueous solution with low osmolality to render them isotonic with blood and suitable for intravenous injection. Alternatively, these formulations can be diluted with a placebo that has the same composition as the formulation but does not contain the active drug and may be prepared by the same process that is utilized to prepare the formulation containing active drug.

In another embodiment, this invention comprises an injectable pharmaceutical composition comprising a dispersion of micrometer to submicrometer size solid particles in an aqueous carrier solution of one or more pharmaceutically acceptable tonicity modifier agents, the particles comprising: a camptothecin drug, a first coating of not more than 10% w/w of a substantially water-insoluble, pharmaceutically acceptable lipophilic agent in which the camptothecin drug is insoluble or poorly soluble, and a second coating of at least one membrane-forming surface stabilizing amphipathic lipid, wherein the dispersion does not aggregate, flocculate, or agglomerate, and the particles do not grow in size above a volume weighted mean diameter of ten micrometers upon steam sterilization and storage prior to administration to a patient.

In another embodiment, this invention comprises an injectable pharmaceutical composition comprising a dispersion of micrometer to submicrometer size solid particles in an aqueous carrier solution of one or more pharmaceutically acceptable tonicity modifier agents, the particles comprising: a camptothecin drug, and a coating of at least one membrane-forming surface stabilizing amphipathic lipid, wherein the dispersion does not aggregate, flocculate, or agglomerate, and the particles do not grow in size above a volume weighted mean diameter of ten micrometers upon steam sterilization and storage prior to administration to a patient.

In the above embodiments, the camptothecin drug can be present in amounts of up to about 25% w/w, preferably in amounts of from about 0.05% w/w to about 5% w/w, more preferably in amounts of from about 0.1% w/w to about 1% w/w, and most preferably in an amount of about 0.2% w/w.

A. Selection of the Membrane-Forming Lipids for Surface Stabilization

The primary requirement for lipids used in the compositions of the present invention is that the surface stabilizing lipid be membrane-forming. This is satisfied by lipids which can, in the presence of excess water, make bilayer structures of the type that is well-documented for phospholipid vesicles or liposomes or which can, in the presence of excess water, make monolayers by self aggregation. This requirement is typically not satisfied by fats and oils such as triglycerides (vegetable oils, tristearin, "fats"). A secondary requirement is that the lipid not have a proclivity for converting into micellar structures at the concentrations used in this invention. This excludes phospholipids of short chain length (6 or less) or lyso-lecithin (containing a single fatty acyl chain). High stability of the membrane forming surface stabilizing material in membrane form is desirable to keep the drug material from rearranging into macroscopic crystals.

In addition to the requirement that the particle surface stabilizing coating be membrane forming and not readily form micelles, the coating must also protect the camptothecin compound from interaction with water that would lead to α-hydroxy lactone hydrolysis, especially during formation of the particle, during the sterilization step in the formation of the dosage form, and during storage after the sterilization step and prior to administration of the camptothecin drug in the dosage forms of this invention.

The following list provides examples of membrane-forming lipids which may be used to form microparticles according to the present invention. This list is only intended to be illustrative.

1. Primary phospholipids:
   Lecithin
   Phosphatidyl choline
   Sphingomyelin
   Synthetic zwitterionic phospholipids or phospholipid analogues 2. Phospholipids capable of calcium-dependant aggregation:
   Phosphatidic acid
   Phosphatidyl serine
   Phosphatidyl inositol
   Cardiolipin (disphosphatidyl glycerol)
   Phosphatidyl glycerol 3. Phosphatidyl ethanolamine 4. Cholesterol and steroids 5. Semi-lipoidal molecules:
   Stearylamine or other long-chained alkyl amines (including primary, secondary, tertiary or quaternary substituted).
   Fatty acids 6. Membrane-active agents, glycolipids and glycoproteins:
   Nystatin
   Amphotericin B
   Gramicidin
   Glycolipids or glycoproteins 7. Mono-glycerides.
   1-monopalmitoyl-(rac)-glycerol (Monopalmitin)
   1-monocaprylol-(rac)-glycerol (Monocaprylin)
   1-monooleoyl-(rac)-glycerol (C18:1, cis-9) (Monoolein)
   1-monostearyl-(rac)-glycerol (Monostearin)

8. Commercially Available Membrane-Forming Lipids:
   Several forms of lecithin (egg lecithin (Pfanstiehl Laboratories); bovine heart lecithin; soy bean lecithin; synthetic lecithin, preferably with 4 to 19 carbons (Supelco, Inc.); unsaturated lecithins (dioleoyl, dilinoleoyl; beta oleoyl; alpha-palmito beta oleoyl; alpha palmitoyl beta linoleoyl and alpha oleoyl beta palmitoyl), diarachidonyl lecithin.

Phosphatidic acid available from egg or as synthetic compounds (dimyristoyl, dipalmitoyl or distearoyl, Calbiochem). Bovine phosphatidyl senna (Supelco or Calbiochem).

Phosphatidyl inositol available from plant (Supelco) or bovine (Calbiochem) sources.

Cardiolipin available (Supelco) from bovine or bacterial sources.

Phosphatidyl glycerol available from bacterial sources (Supelco) or as synthetic compounds (dimyristoyl or dipalmitoyl; Calbiochem).

Phosphatidyl ethanolamine available as egg, bacterial, bovine or plasmalogan (Supelco) or as synthetic compounds diotadecanoyl and dioleoyl analogues and dihexadecyl, dilauryl, dimyristoyl and dipalmitoyl (Supelco and Calbiochem).

Monoglycerides available from Sigma Chemical Co. (1-monopalmitoyl-(rac)-glycerol, monopalmitin; 1-monocaprylol-(rac)-glycerol, monocaprylin; 1-monooleoyl-(rac)-glycerol (C 18:1, cis-9), monoolein; 1-monostearyl-(rac)-glycerol, monostearin).

In preferred embodiments of this invention, the membrane-forming amphipathic lipid can be present in amounts of from 0.2% w/w to about 5% w/w, preferably in amounts of from 1% w/w to about 5% w/w, and more preferably in amounts of about 4% w/w.

In another embodiment, compositions of this invention can comprise a membrane forming lipid together with one or more than one other surface active agent wherein combinations are chosen such that they fulfill the primary criteria of monolayer or bilayer membrane formation in presence of excess of water and the secondary criteria that the selected combination does not convert into micellar structures at the concentrations used in this invention.

When compositions of this invention comprise a membrane forming lipid together with one or more than one other surface active agent, in addition to the requirement that the particle surface stabilizing coating formed in the presence of the other surface active agent be membrane forming and not readily form micelles, the coating must also protect the camptothecin compound from interaction with water that would lead to α-hydroxy lactone hydrolysis, especially during formation of the particle, during the sterilization step in the formation of the dosage form, and during storage after the sterilization step and prior to administration of the camptothecin drug in the dosage forms of this invention.

Surface active agents with high HLB numbers such as PEG-containing materials that are substantially more hydrophilic and even soluble in water can potentially lead to enhanced access of water to the surface of the particle when used to stabilize the particle. The enhanced access of water to the camptothecin compound can lead to α-hydroxy lactone hydrolysis to form hydroxy acid compounds which are substantially less active in therapeutic applications such as the treatment of cancer and other indications of the α-hydroxy lactone-containing camptothecin compounds, and which are more toxic to healthy tissue than the α-hydroxy lactone-containing camptothecin compounds. Thus, the amount of added other surface active compound should be less than the amount that would lead to hydrolysis of the α-hydroxy lactone ring during formation of the particle, during sterilization, and during storage prior to use.

Representative surface active agents that can be present as long as the membrane forming property of the lipid is not compromised include the following materials.

1. Nonionic surfactants
    Examples include polyoxyethylene fatty alcohol ethers, sorbitan fatty acid esters, polyoxyethylene sorbitan fatty acid esters, sorbitan esters, glycerol esters such as and glycerol triacetate, polyethylene glycols, cetyl alcohol, cetostearyl alcohol, stearyl alcohol, poloxamers, polaxamines, polyoxethylene castor oil derivatives, vitamin E or its derivatives, such as D-alpha-tocopheryl polyethylene glycol 1000 succinate, PEG glyceryl fatty acid esters such as PEG-8 glyceryl caprylate/caprate, PEG-4 glyceryl caprylate/caprate, PEG-32 glyceryl laurate, PEG-6 glyceryl mono oleate, PEG-6 glyceryl linoleate, propylene glycol mono- and di-fatty acid esters, such as propylene glycol laurate, propylene glycol caprylate/ caprate; also diethylene glycol monoethyl ether, sorbitan fatty acid esters, monoglycerides and acetylated monoglycerides, e.g., glycerol monooleate, glycerol monostearate and mono-and di- acetylated monoglycerides, monoacetin, and diacetin; polyethylene glycol (PEG) such as PEG 300, PEG 400, PEG 600, PEG 1000, PEG 1500, PEG 3400.
2. Anionic surfactants
    Examples include bile salts, potassium laurate, triethanolamine stearate, sodium lauryl sulfate, alkyl polyoxyethylene sulfates, sodium alginate, dioctyl sodium sulfosuccinate, sodium carboxymethylcellulose, and calcium carboxymethylcellulose.
3. Cationic surfactants
    Examples include quaternary ammonium compounds, benzalkonium chloride, cetyltrimethylammonium bromide, and lauryldimethylbenzyl-ammonium chloride.
4. Substituted cellulose derivatives
    Examples include methylcellulose, hydroxycellulose, hydroxy propylcellulose, hydroxy propylmethylcellulose, noncrystalline cellulose, sodium carboxymethyl cellulose.

Optionally, a small quantity of one or more low-molecular weight hydrophilic substances, for example, monohydric or polyhydric alcohols, such as ethanol or glycols or glycerol may be also added in the surface modifiers as long as the membrane forming properties of the lipid surface stabilizing agent are not compromised and α-hydroxy lactone hydrolysis in the camptothecin compound does not ensue. A detailed description of these surface modifying agents and lipophilic or hydrophobic media may be found in Remington's Pharmaceutical Sciences, 18th Edition, 1990, Mack Publishing Co., PA; and Theory and Practice of Industrial Pharmacy, Lachman et al., 1986 and many monographs published thereafter.

It is possible to add other constituents to increase the stability of preferred embodiments of this invention or to modify the rate of release of the camptothecin such as at a site of therapeutic action. For example, pharmacologically-acceptable oils can be added at low weight concentration to facilitate contact between the camptothecin micrometer to submicrometer size particle surface and its protective membrane forming amphipathic lipid layer. It is necessary that the type of oil and in weight concentration be chosen such that the crystalline drug not be dissolved by the oil and that the coating by the membrane-forming lipid not be disrupted. These relationships can be determined empirically. Useful oils include, but are not limited to, vitamin E, isopropyl myristate, benzyl benzoate, oleyl alcohol, mineral oil, squalene and vegetable oil. The addition of these other constituents should not lead to enhancement in hydrolysis of the α-hydroxy lactone ring of the camptothecin compound in the compositions of this invention during formation of the particles, during sterilization, and during storage prior to use.

It is also possible to "precoat" the freshly formed micrometer to submicrometer size particles of camptothecin drugs by non-aqueous agents that are non-antigenic and compatible with surface stabilizing monolayer or bilayer membrane forming amphipathic agents. Useful agents include phospholipid-compatible, non-antigenic molecules which are solid at 37° C. Examples include paraffin, tristearin, ethyl oleate, cetostearyl alcohol, cetyl alcohol, myristyl alcohol, stearyl alcohol and petrolatum. For example, these materials can be incorporated onto the freshly formed micrometer to submicrometer size particles of camptothecin drugs by sonication or shear. Stabilization can be achieved by adding surface stabilizing monolayer or bilayer membrane forming amphipathic agents during the particle size reduction process. It is desirable to use low weight concentrations (less than 10%) such that the payload is not degraded, and the rate or dissolution of the drug is not unduly impeded. Also, biodegradability may impose a further limitation. The use of these agents should not lead to enhancement in hydrolysis of the α-hydroxy lactone ring of the camptothecin compound in the compositions of this invention during formation of the particles, during sterilization, and during storage prior to use.

In one embodiment, preferred non-aqueous agents that can be used to precoat freshly formed micrometer to submicrometer size particles of camptothecin drugs can be selected as individual compounds or combination of compounds from the following group of compounds in which the camptothecin drug is either insoluble or poorly soluble, such as from the group of hydrophobic components such as triglycerides, diglycerides, monoglycerides, saturated or unsaturated free fatty acids, mixtures of saturated and unsaturated free fatty acids, and fatty acid, their esterification and their transesterification products obtained by reacting with alkanols, glycols, glycerol, or cholesterol. Examples of such hydrophobic components include but are not limited to propylene glycol dicaprylate/caprate, caprilic/capric triglyceride, caprylic/capric/linoleic triglyceride, e.g. synthetic medium chain triglycerides having $C_{8-12}$ fatty acid chains or other derivatized (synthetic) triglycerides of the type known and commercially available under Miglyol 810, 812, 818, 829 and 840. Additional examples include oils from biological sources such as vegetable oils and fish oils such as soybean oil, almond oil, sunflower oil, olive oil, corn oil, polyunsaturated oils, saturated hydrogenated oils, fish oils, omega-3 oils, omega-6 oils and $C_{12-18}$ fatty acid mono-, di- and triglycerides prepared by individual admixing or as transesterification products of vegetable oils or fish oils (such as soybean oil, almond oil, sunflower oil, olive oil, corn oil, polyunsaturated oils, saturated hydrogenated oils, omega-3 oils, omega-6 oils) with glycerol.

Additional non-aqueous agents that may be used for precoating include pharmaceutically acceptable non-aqueous solvents in which the camptothecin drug is either insoluble or poorly soluble. These solvents may be selected from the classes of organic chemicals such as, but not limited to, monohydric alcohols e.g. alkanols; dihydric alcohols e.g., glycols; polyhydroxy compounds e.g., glycerin; aromatic esters, e.g., benzyl benzoate, diethyl phthalate, propyl gallate; non-aromatic esters such as triacetin, diacetin, monoacetin, triethyl citrate; water soluble organic solvents such as propylene carbonate and glycofurol, dimethyl isosorbide, dimethyl isoidide, dimethyl isomannide, and other pharmaceutically suitable hydrophobic compounds that remain in liquid state at ambient temperature and pressure such as hydrofluorocarbons such as perflubron.

When preparing the composition for injection, particularly for intravenous delivery, the continuous phase preferably comprises an aqueous solution of tonicity modifiers, buffered to a pH below 7, more preferably below 6. The tonicity modifier is preferably selected from sodium chloride, glucose, mannitol, trehalose, glycerol, or other pharmaceutically agent that renders the osmotic pressure of the formulation isotonic with blood. Alternatively, when a larger quantity of the tonicity modifier is used in the formulation, it can be diluted prior to injection with a pharmaceutically acceptable diluent to render the mixture isotonic with blood.

Optionally, preservatives can be added. These include, but are not limited to, benzalkonium chloride, propylparabem, butylparaben, chlorobutanol, benzyl alcohol, phenol, sodium benzoate, EDTA, etc. as long as the membrane forming property of the lipid material is not compromised. The addition of preservatives should not lead to enhancement in hydrolysis of the α-hydroxy lactone ring of the camptothecin compound in the compositions of this invention during formation of the particles, during sterilization, and during storage prior to use.

B. Surface Stabilized Microdroplet Dispersion of a Camptothecin

According to another pharmaceutical composition category according to the present invention, the composition comprises a phospholipid microdroplet suspension of a camptothecin, preferably 9-nitro-camptothecin. Procedures for making this category of pharmaceutical composition, as well as varying embodiments, are described in U.S. Pat. Nos. 4,622,219 and 4,725,442, which are each incorporated by reference.

In a preferred embodiment, the composition comprises a phospholipid stabilized aqueous dispersion of microdroplets of pharmaceutically acceptable lipophillic liquid which sequesters a camptothecin, preferably 9-nitro-camptothecin. The composition is preferably stabile to sterilization and is preferably sterilized, most preferably by steam sterilization.

In this aspect of the invention, the components of the dispersions should not permit hydrolysis of the α-hydroxy lactone ring of the camptothecin compound during formation of the microdroplets, during sterilization, and during storage prior to use.

In one embodiment according to this category, the pharmaceutical composition comprises microdroplets having a mean diameter less than one micron, and optionally between 200 Angstroms and one micron, the droplets comprise a substantially water-insoluble, pharmacologically acceptable liquid containing a camptothecin surrounded by a layer comprising a phospholipid.

In a preferred aspect of this embodiment, the pharmaceutical composition comprises a sterilized aqueous dispersion of microdroplets, preferably steam sterilized, suitable for injection, having a mean diameter less than one micron, and optionally between 200 Angstroms and one micron, the microdroplets comprise a substantially water-insoluble, pharmacologically acceptable lipophillic liquid vehicle, dissolved within which a camptothecin drug and at least one membrane-forming amphipathic lipid, surrounded by a layer comprising at least one membrane-forming amphipathic lipid, preferably a phospholipid, with the microdroplets being dispersed in a continuous phase of a carrier aqueous solution of pharmaceutically acceptable tonicity modifier agents.

As discussed elsewhere, the continuous aqueous phase of the microdroplet dispersion composition is preferably acidic, i.e., have a pH less than 7 in order to minimize hydrolysis of the α-hydroxy lactone ring of camptothecins mediated by hydroxyl species such as can occur in base catalyzed hydrolysis. In a more preferred embodiment, the aqueous component of the composition has a pH less than 6.5, more preferably less than 6. Optionally, the pH of the aqueous component of the composition is between 5 and 7, more preferably between 5 and 6.5 and most preferably between 5 and 6.

Examples of pharmaceutically acceptable water-insoluble, lipophilic liquid vehicles include, but are not limited to alkanes, dialkyl ethers, long-chain esters, hydrophobic esters, biocompatible silicones, biocompatible high molecular weight fluorocarbons, oil-soluble vitamins and biocompatible volatile liquid anesthetics. For intravenous injection use, preferred liquids include biocompatible long-chain esters, biocompatible hydrophobic esters, biocompatible high molecular weight fluorocarbons, oil-soluble vitamins and biocompatible liquid anesthetics.

The pharmaceutical composition is preferably an isotonic solution. In this regard, the composition preferably further includes tonicity modifiers, such as mannitol, glycerol, physiological saline, and/or trehalose.

The ratio of volume of the pharmacologically acceptable liquid containing a camptothecin to the weight of the phospholipid layer is preferably at least 1.0 ml/g.

Some advantages believed to be provided by the microdroplet composition include protection of the α-hydroxy lactone functional group from hydrolysis in aqueous media, a relatively slow release of the camptothecin compound to the tissues, and potential for a targeted delivery to diseased tissues and cells by intelligent choice of the site of injection with concomitant lowered metabolic degradation, first pass effects, and toxic side-effects in the liver and other organs.

A preferred method of preparing microdroplet dispersions is by sonication with a probe sonicator. Alternatively, microdroplets can be prepared in a bath sonicator. For small scale preparations a 1.0 cm diameter test tube is suspended, with use of a test-tube clamp, in a bath sonicator filled with water. The components of the microdroplet (lipophillic phase, phospholipid or membrane-forming amphipathic lipids, tonicity modifier, pH buffering agent, and drug to be included) are first grossly mixed by shaking, Vortex mixing, Polytron or other methods. The homogenized suspension is then introduced into a bath sonicator and sonicated for 1–2 hours. If the preparation is to be done on a large scale, it will be possible to omit the test tube and introduce the components of the microdroplet dispersion directly into the bath sonicator.

Microdroplet dispersions may also be produced by high intensity mechanical agitation. Useful methods include use of a Waring blender, a Polytron and high frequency shakers such as a commercial paint shaker.

An alternative method is a solvent dilution method. The desired constituents of the microdroplets are dissolved at high concentration in ethanol or another oil- and water-miscible organic liquid. The ethanol solution is rapidly diluted into an aqueous solution containing tonicity modifier and pH buffering agents with vigorous mechanical agitation to insure rapid mixing. The ethanol dissolves in the aqueous phase while the other constituents do not. The finely-dispersed constituents spontaneously form microdroplet dispersions; the ethanol can be conveniently removed for example by dialysis or by means of vacuum evaporation or distillation.

Microdroplet dispersions can also be formed by a process similar to spray painting. The water-insoluble and oil-soluble constituents of a microdroplet dispersion formulation of this invention are suspended together and sucked into the intake of a commercial spray forming device and the resulting output spray can be directed through an aqueous solution containing tonicity modifier(s) and pH buffering agents to form a microdroplet dispersion. The spray can be directed through the aqueous solution from below the surface of the solution or from above the surface of the aqueous solution, optionally through a gas such as a fluorocarbon or sulfur hexafluoride or carbon dioxide optionally containing volatilized or atomized lipid molecules and optionally at a temperature above the temperature of the aqueous phase to potentially modify the surface properties of microdroplet through adsorption or absorption of components of the gas.

In a preferred embodiment, a preferred composition can be obtained according to this invention by first forming an aqueous-phase in the form of a solution by dissolving the water soluble components such as pH buffering agents and tonicity modifiers in a required quantity of water. Mannitol and trehalose are known to modify the osmotic pressure to provide osmolalities of the suspensions suitable for intravenous injection. A suitable osmolality is one for example that is substantially isotonic with blood. Preferably, a pharmaceutically acceptable pH buffering agent is used. A particularly preferred pH buffering agent is sodium acetate/acetic acid.

In parallel, an oil-phase may be prepared by dissolving desired quantities of a camptothecin such as 9-nitro-camptothecin and one or more membrane-forming amphipathic lipids such as one or more phospholipids for example Lipoid EPC and dimyristoylphosphatidyl glycerol optionally with a membrane enhancing substance such as cholesterol in a required quantity of water-insoluble lipophilic liquid vehicle comprising a synthetic or a natural triglyceride or a mixture thereof, preferably in a desired quantity of a mixture of a medium chain triglycerides and a vegetable oil such as soybean oil. Magnetic stirring is employed to facilitate dissolution. After complete dissolution of all components, the solution is further stirred for at least an additional time to ensure complete solubilization and homogenization of the dissolved components. This oil phase preparation is carried out in an inert atmosphere such as a nitrogen atmosphere.

In a preferred embodiment, the lipophilic liquid vehicle or lipophilic agent is selected from the group consisting of vegetable oils, animal oils, synthetic oils, semi-synthetic oils, soybean oil, medium chain triglycerides, long chain triglycerides, triglycerides of C8 to C12 saturated fatty acids, triglycerides of C14 to C22 saturated fatty acids, triglycerides of C14 to C22 unsaturated fatty acids, and combinations thereof. In addition, cholesterol can be used not only in the lipophilic liquid vehicle and as a lipophilic agent of this invention, but also in the membrane-forming amphipathic lipid.

A pre-mix comprising a mixture of the oil-phase and water-phase may be prepared by transferring the oil-phase under nitrogen pressure into the water-phase and dispersing the mixture by rapid stirring under a nitrogen atmosphere. Sufficient quantity of dilute sodium hydroxide solution or 20% acetic acid solution is added to adjust the pH to 7.5.

The pre-mix dispersion is then subjected to high-pressure homogenization with cooling as needed, preferably under nitrogen and preferably at a maximum pressure in the range of about 7,000 psi to 8,000 psi for a number of volume passes sufficient to achieve a desired droplet size distribution. The homogenized product is filled into vials, stoppered under a nitrogen atmosphere, and autoclaved preferably using terminal steam sterilization for example at 121° C. or hotter for about 15 to about 30 minutes or longer and then cooled.

The volume weighted diameters and particle size distribution of the resulting steam sterilized dispersion are determined with a Nicomp 370 apparatus which utilizes quasi-elastic laser light scattering by the dispersed phase to provide accurate measure of very small articles of as low as a about two micrometers or even smaller.

These dispersions can be further diluted for example with suitable sterile aqueous solution with osmolality isotonic with blood and suitable for injection. Alternatively, these formulations can be diluted with a placebo that has the same composition as the formulation but does not contain the active drug and may be prepared by the same process that is utilized to prepare the formulation containing active drug.

Microdroplet dispersions according to the present invention may be prepared from a wide variety of organic phases (i.e., the substantially water-insoluble, pharmacologically acceptable liquid) which, for convenience, may be considered by the following non-limiting types or categories: alkanes, natural and plant-derived "oils" (e.g., olive oil and various vegetable oils), semisynthetic oils or fully synthetic oils such as triglycerides of fatty acids, ethers (e.g., dipropyl ether, n-dipropyl ether, dibutyl ether, and n-dibutyl ether), esters (e.g., a long-chain or hydrophobic ester), silicones, and high molecular weight liquid fluorocarbons. For intravenous use, microdroplet dispersions according to the present invention may be prepared from a variety of biocompatible organic phases including biocompatible natural and plant-derived oils such as olive oil and various vegetable oils, biocompatible semisynthetic oils or biocompatible fully synthetic oils such as triglycerides of fatty acids, biocompatible fatty acid esters, and biocompatible high molecular weight liquid fluorocarbons.

Preferred agents suitable as substantially water-insoluble, pharmacologically acceptable lipophilic liquid vehicle can be a non-aqueous medium in which the camptothecin drug is either soluble or insoluble or poorly soluble and is selected from the group of hydrophobic components, either individually or in combination, such as triglycerides, diglycerides, monoglycerides, saturated or unsaturated free fatty acids, mixtures of saturated and unsaturated free fatty acids, and fatty acid, their esterification and their transesterification products obtained by reacting with alkanols, glycols, glycerol, or cholesterol. Examples of such hydrophobic components include but are not limited to propylene glycol dicaprylate/caprate, caprilic/capric triglyceride, caprylic/capric/linoleic triglyceride, e.g. synthetic medium chain triglycerides having $C_{8-12}$ fatty acid chains or other derivatized (synthetic) triglycerides of the type known and commercially available under Miglyol 810, 812, 818, 829 and 840. Additional examples include oils from biological sources such as vegetable oils and fish oils such as soybean oil, almond oil, sunflower oil, olive oil, corn oil, polyunsaturated oils, saturated hydrogenated oils, fish oils, omega-3 oils, omega-6 oils and $C_{12-18}$ fatty acid mono-, di- and triglycerides prepared by individual admixing or as transesterification products of vegetable oils or fish oils (such as soybean oil, almond oil, sunflower oil, olive oil, corn oil, polyunsaturated oils, saturated hydrogenated oils, omega-3 oils, omega-6 oils) with glycerol.

In selecting water insoluble liquids of this invention, care must be taken to avoid liquids which can lead to facilitation of hydrolysis of the α-hydroxy lactone ring of the camptothecin compound during preparation of the microdroplet dispersion, during sterilization of the microdroplet disperison, and during storage of the microdroplet dispersion prior to use.

In another embodiment, additional non-aqueous media include pharmaceutically acceptable non-aqueous media or solvents in which the camptothecin drug is either soluble or insoluble or poorly soluble. These solvents may be selected from classes of organic chemicals such as but not limited to, monohydric alcohols e.g., alkanols; dihydric alcohols e.g., glycols; polyhydroxy compounds e.g., glycerin; aromatic esters, e.g., benzyl benzoate, diethyl phthalate, propyl gallate; non-aromatic esters such as triacetin, diacetin, monoacetin, triethyl citrate; water soluble organic solvents such as propylene carbonate and glycofurol, dimethyl isosorbide, dimethyl isoidide, dimethyl isomannide, and other pharmaceutically suitable hydrophobic compounds that remain in liquid state at ambient temperature and pressure such as hydrofluorocarbons such as perflubron. In selecting these non-aqueous media, care must be taken to avoid media which can lead to facilitation of hydrolysis of the α-hydroxy lactone ring of the camptothecin compound during preparation of the microdroplet dispersion, during sterilization of the microdroplet disperison, and during storage of the microdroplet dispersion prior to use. Compounds that readily irreversibly react with the camptothecin α-hydroxy lactone to form an inactive camptothecin compound are also to be avoided unless used in substantially small amounts so that the camptothecin compound remains substantially intact in the α-hydroxy lactone form Optionally, small quantity of low-molecular weight lipid soluble substances, for example, monohydric or polyhydric alcohols, such as ethanol or glycols or glycerol may be also added in the non-aqueous medium for the vehicle. In selecting these low molecular weight substances, care must be taken to avoid substances which can lead to facilitation of hydrolysis of the α-hydroxy lactone ring of the camptothecin compound during preparation of the microdroplet dispersion, during sterilization of the microdroplet disperison, and during storage of the microdroplet dispersion prior to use. Compounds that readily irreversibly react with the camptothecin α-hydroxy lactone to form an inactive camptothecin compound are also to be avoided unless used in substantially small amounts so that the camptothecin compound remains substantially intact in the α-hydroxy lactone form.

Various membrane-forming amphipathic lipids described above for use in preparing the surface stabilized micrometer to submicrometer size solid particulate dispersion of camptothecin drugs are suitable for use in preparing the microdroplet dispersions of the present invention. Mixtures of two or more such lipids are useful to vary the surface properties and reactivity. Examples of lipids that may be used, include, but are not limited to lecithin, phosphatidylcholine, sphingomyelin, phosphatidic acid, phosphatidyl serine, phosphatidyl inositol, cardiolipin (diphosphatidyl glycerol), phosphatidyl glycerol, phosphatidyl ethanolamine, positively or negatively charged phospholipids, electroneutral phospholipids, natural phospholipids, semisynthetic phospholipids or fully synthetic phospholipids, saturated phospholipids, unsaturated phospholipid, and combinations thereof; steroids such as cholesterol and estrogens (e.g., estirol, estrone, estradiol and diethylstilbestrol), androgens such as androstenedione and testosterone, semi-lipoidal molecules which can incorporate into the monolayer and change the surface activity of the microdroplet, such as stearylamine or other long-chained alkyl amines which can be primary or secondary, but preferably non reacting hindered or non nucleophilic amines such as hindered primary, secondary, tertiary or quaternary substituted, arachidonic acid or fatty acids, and membrane-active agents including nystatin, amphotericin B and gramicidin. In selecting these substances, care must be taken to avoid substances which can lead to facilitation of hydrolysis of the α-hydroxy lactone ring of the camptothecin compound during preparation of the microdroplet dispersion, during sterilization of the microdroplet disperison, and during storage of the microdroplet dispersion prior to use. Compounds that readily irreversibly react with the camptothecin α-hydroxy lactone to form an inactive camptothecin compound are also to be avoided unless used in substantially small amounts so that the camptothecin compound remains substantially intact in the α-hydroxy lactone form.

In regard to lecithin, several forms may be used. For example lecithin is available as egg or bovine heart lecithin (natural) or in several synthetic varieties which differ in chain length. These include chain lengths ranging from 4 to 19 carbons (Supelco, Inc.). It is believed that lecithins with chain lengths in the biological range (10–18 carbons) are useful in various applications. Specific examples of lecithins include dimyristoyl (14 carbons), and didodecanoyl (12 carbons).

Unsaturated lecithins (dioeoyl), dilinoeoyl; alpha-palmito, beta oleoyl; alpha palmitoyl beta linoleoyl and alpha oleoyl beta palmitoyl) are also available. Diarachidonyl lecithin (highly unsaturated and a prostaglandin precursor) is also available, as is alpha palmito beta myristoyl (mixed unsaturated chains) lecithin. Phosphatidic acid is available from egg or as synthetic compounds (dimyristoyl, dipalmitoyl or distearoyl, Calbiochem). Bovine phosphatidyl serine is available (Supelco or Calbiochem). Phosphatidyl inositol is available from plant (Supelco) or bovine (Calbiochem) sources. Cardiolipin is available (Supelco) from bovine or bacterial sources. Phosphatidyl glycerol is available from bacterial (Supelco) sources or as synthetic compounds (dimyristoyl or dipalmitoyl; Calbiochem). Phosphatidyl ethanolamine is available as egg, bacterial, bovine, or plasmalogen (Supelco) or as synthetic compounds dioctadecanoyl and dioleoyl analogues and dihexadecyl, dilauryl, dimyristoyl and dipalmitoyl (Supelco and Calbiochem). A number of natural and synthetic phospholipids useful in this invention are also available from Avanti Polar Lipids and from Lipoid GmbH.

Preferred membrane forming lipids include natural and synthetic lipids such as hen egg-derived phospholipid (egg phospholipid and purified egg phospholipid), soy phospholipid, dimyristoyl lecithin, didodecanoyl lecithin, dioeoyl lecithin, dilinoeoyl lecithin, alpha-palmito-beta-oleoyl lecithin, alpha-palmitoyl-beta-linoleoyl lecithin, alpha-oleoyl-beta-palmitoyl lecithin, diarachidonyl lecithin, alpha-palmito-beta-myristoyl lecithin, dimyristoyl phosphatidic acid, dipalmitoyl phosphatidic acid, distearoyl phosphatidic acid, phosphatidyl serine, phosphatidyl inositol, dimyristoyl phosphatidyl glycerol or dipalmitoyl phosphatidyl glycerol, dioctadecanoyl phosphatidyl ethanolamine, dioleoyl phosphatidyl ethanolamine, dihexadecyl phosphatidyl ethanolamine, dilauryl phosphatidyl ethanolamine, dimyristoyl phosphatidyl ethanolamine, dipalmitoyl phosphatidyl ethanolamine, Lipoid E80, Lipoid ES, Lipoid 90H, and Lipoid 100H. A particularly preferred membrane forming lipid is Lipoid E80.

In one embodiment, the invention comprises an injectable pharmaceutical composition comprising a dispersion in an aqueous carrier solution of one or more pharmaceutically acceptable tonicity modifier agents of micrometer to submicrometer size spherical liquid droplets of a substantially water-insoluble, pharmaceutically acceptable lipophilic liquid vehicle containing in a dissolved form a camptothecin drug and at least one membrane-forming amphipathic lipid, the liquid droplets being surrounded by a layer comprising at least one membrane-forming amphipathic lipid, wherein upon steam sterilization and storage prior to administration to a patient, the dispersion does not aggregate, flocculate, agglomerate, or coalesce, and the droplets do not grow in size above a volume weighted mean diameter of ten micrometers.

In another embodiment, the invention comprises an injectable pharmaceutical composition comprising an aqueous carrier solution of one or more pharmaceutically acceptable tonicity modifier agents, said solution containing a dispersion of spherical liquid droplets of a first size distribution of a substantially water-insoluble, pharmaceutically acceptable lipophilic liquid vehicle, said vehicle containing solid particles of a camptothecin drug of a second size distribution together with the camptothecin drug in a dissolved form and at least one membrane-forming amphipathic lipid, the liquid droplets being surrounded by a layer comprising at least one membrane-forming amphipathic lipid, wherein the first size distribution is in the range of submicrometer to micrometers, and the second size distribution is smaller than the first size distribution, and wherein upon autoclave sterilization and storage prior to administration to a patient, the dispersion does not aggregate, flocculate, agglomerate, or coalesce, and the droplets do not grow in size above a volume weighted mean diameter of ten micrometers.

In these embodiments, the lipophilic liquid vehicle can be present in amounts up to about 40% w/w, preferably in amounts up to about 25% w/w, and more preferably in amounts up to about 20% w/w. In preferred embodiments, the lipophilic liquid vehicle is present in amounts greater than 0.5% w/w.

In preferred embodiments of this invention, the ratio of phospholipid to camptothecin compound in the suspension is less than 150, preferably less than 100, more preferably less than 50, even more preferably less than 20, yet even more preferably less than 10, more preferably less than 5, and most preferably less than 1. In a preferred embodiment, when preparing the composition for injection, particularly for intravenous delivery, the continuous phase is an aqueous solution of tonicity modifiers, buffered to a pH below 7, more preferably below 6. The tonicity modifier is selected from sodium chloride, glucose, mannitol, trehalose, glycerol, or other pharmaceutically agent that renders the osmotic pressure of the formulation isotonic with blood. Alternatively, when a larger quantity of the tonicity modifier is used in the formulation to produce a hypertonic dispersion prior to use, it can be diluted prior to injection with a pharmaceutically acceptable diluent to render the mixture isotonic with blood.

Optionally, preservatives can be added. These include, but are not limited to, benzalkonium chloride, propylparabem, butylparaben, chlorobutanol, benzyl alcohol, phenol, sodium benzoate, EDTA, etc. In selecting these substances, care must be taken to avoid substances which can lead to facilitation of hydrolysis of the -hydroxy lactone ring of the camptothecin compound during preparation of the microdroplet dispersion, during sterilization of the microdroplet disperison, and during storage of the microdroplet dispersion prior to use. Compounds that readily irreversibly react with the camptothecin -hydroxy lactone to form an inactive camptothecin compound are also to be avoided unless used in substantially small amounts so that the camptothecin compound remains substantially intact in the α-hydroxy lactone form.

The type and amount of membrane forming amphipathic agents and other ingredients used is based on the relative solubility and/or polarity of these ingredients, as well as their mutual compatibility. The formulation compositions may be optimized with respect to each composition individually. Compositions in accordance with the present invention may include additional ingredients, for example, diluents or bulking agents, anti-oxidants, preserving agents, and pH buffering agents. In selecting these substances, care must be taken to avoid substances which can lead to facilitation of hydrolysis of the α-hydroxy lactone ring of the camptothecin compound during preparation of the microdroplet dispersion, during sterilization of the microdroplet disperison, and during storage of the microdroplet dispersion prior to use. Compounds that readily irreversibly react with the camptothecin α-hydroxy lactone to form an inactive camptothecin compound are also to be avoided unless used in substantially small amounts so that the camptothecin compound remains substantially intact in the α-hydroxy lactone form.

Without wishing to limit this invention by being bound by a particular theory of its operation, it is thought that the combination of membrane forming amphipathic surface active agents or lipophilic oily vehicle and non-surface active water soluble agents perform several useful functions. These functions are believed to include suppression the process of Ostwald Ripening during the cooling cycle of the terminal steam sterilization (vide infra) and therefore maintain the particle size, increase the storage stability, minimize sedimentation, and decrease the particle growth during lyophilization and reconstitution.

The association between the surface modifier and the drug particles is believed to be enhanced such that the protecting environment around the particles is maintained over a wide range of temperature and pressure as is prevalent during the terminal steam sterilization process and substantially minimizing hydrolysis of the α-hydroxy lactone ring during autoclaving.

The interface compatibility between water-insoluble dispersed drug particles or dispersed lipophillic droplet surface and the continuous aqueous medium is believed to be enhanced by the present invention.

The present invention is also believed to aid in orienting the surface modifiers' hydrophilic portion preferentially into the aqueous phase while the lipophilic portion remains strongly adsorbed onto the surface of the water-insoluble drug particle or the surface of lipophillic microdroplet as well as to enhance the stability of such orientation.

It is further thought that the improved in-vivo efficacy of camptothecin drugs in the formulations of the present invention is at least partially due to sequestering of the majority of the drug substance in the form of solid particle or in the dissolved state in an oily vehicle with the aid of combination of surface active agents or lipophilic oily vehicle and non-surface active water soluble agents in such a way that the camptothecin drug molecules are not substantially available to high affinity protein binding sites that can destabilize the active α-hydroxy lactone form of the drug within an in-vivo environment.

Emphasizing again that there is no intention of restricting this invention to any theory, cholesterol, triglycerides (in the form of natural or synthetic triglycerides) and phospholipids, that are present in the preferred embodiments of this invention, may be required by rapidly proliferating neoplastic cells for their cellular functions. The compounds thus may serve to facilitate preferential uptake of the components of these formulations by these cells.

It is also believed that the in-vivo efficacy of camptothecin drugs demonstrated herein arise from the combination of surface active agents or lipophilic oily vehicle and non-surface active water soluble agents helping to preserve the camptothecin drug molecules in an active α-hydroxy lactone form in therapeutically effective quantities in a therapeutically effective timeframe during their delivery to the target sites of the neoplastic cells to cause lethal damage to these cells.

C. Sterilization of Camptothecin Formulations

Formulations of camptothecin and camptothecin derivatives such as 9-nitro-camptothecin suitable for intravenous administration need to be sterilizable. Prior to administration, the compositions of this invention must undergo a sterilization step. Two common methods for sterilization of formulations suitable for injection are described herein.

In one scenario, a formulation can be generated under aseptic conditions using components or mixtures of components that are each sterilized prior to preparation of the final formulation and container filling such as filling of a vial and sealing or capping the file. This method may be desirable when one or more components of the formulation is subject to chemical modification such as hydrolysis of a α-hydroxy lactone ring or when the formulation such as a liposome is unstable to commonly used methods of sterilization such as thermal autoclaving or treatment with steam for a time sufficient to destroy any trace quantities of contaminating organism. However, this method is generally expensive to perform, requiring great care to exclude contaminants prior to final sealing of the dosage form, the creation and maintenance of an aseptic environment, and the manipulation of ingredients and process conditions under aseptic conditions to generate a desired sterile formulation.

It is more desirable to prepare a composition, seal it in a vial, and autoclave it such as with the use of steam applied to the vial above the boiling point of water such as at or above 121° C. for a time such as about 15 to 20 minutes or longer to ensure the destruction of any trace amount of contaminating organism. The sealed vial may then cooled and stored at a suitable temperature ready for use.

A preferred method of thermal sterilization of a composition of this invention comprises heating the composition in a vial with steam to at least 121° C. for at least 15 minutes.

Thermal sterilization of the composition post formulation is simpler to accomplish and relatively less expensive than one requiring pre-sterilization of all components and manipulation of ingredients in a totally aseptic environment. It is also a generally preferred method of sterilization in the pharmaceutical industry. However, in an aqueous medium labile chemical functional groups that may be present in constituents of the formulation can potentially react with water under elevated temperature conditions. In addition, species that may be present in a formulation in an aqueous medium such as hydroxyl ions, protons, nucleophilic species such as carboxylate ions, metal ions and chelated metal ions even in trace quantities can potentially catalyze the reaction with water of labile chemical functional groups that may be present. Such catalysts generally require the functional group to be accessible to them, for example in the form of a part of a molecule that is dissolved in a solvent or otherwise entropically free to react with water. Examples of potentially labile functional groups include α-hydroxy lactones (i.e., cyclic esters) such as the one present in camptothecins, which can hydrolyze in water to form alcohols and carboxylic acids, certain labile carboxylic acid esters which can hydrolyze in water to form alcohols and carboxylic acids and/or carboxylates especially in the presence of a catalyst, and phosphate esters which can hydrolyze in water to form alcohols and phosphoric acids and/or phosphates. Additionally, compositions containing small drug particles in the nanometer and micron size distribution range that is acceptable for injection when in that size range can potentially increase in size because of Ostwald ripening under stress conditions such as under mechanical stress by shaking, and under thermal stress such as by increasing and decreasing the temperature of the formulation or by applying temperature gradients to the formulation. In addition, suspensions of particles can also show time and/or temperature dependent instability that results in irreversible agglomeration of particles to give effectively larger size distributions, and coagulation of components to give precipitates that cannot be resuspended with mild shaking or with gentle swirling. The micrometer to submicrometer size particles of a particulate dispersion dosage forms may also suffer from irreversible aggregation upon steam sterilization stress. Similarly, the micrometer to submicrometer size droplets of a microdroplet dispersion dosage forms may also suffer from irreversible coalescence upon steam sterilization stress. Furthermore, if a formulation is frozen and then thawed, the stress of such a process may frequently lead to irreversible precipitation and coagulation of some or all of the components.

WO 99/61001, which is incorporated by reference in its entirety, describes processes for thermally sterilizing certain aqueous suspensions of phospholipid stabilized particles. The processes described in WO 99/61001 are particularly useful for sterilizing suspensions of small particles after they are placed in vials and sealed prior to use. These processes may be used to heat sterilize the aqueous formulations according to the present invention.

As demonstrated in the examples herein, the heat sterilized pharmaceutical compositions of the present invention where shown to be stable under various storage conditions that might be encountered after sterilization during a storage time prior to administration. The heat sterilized pharmaceutical compositions of the present invention where shown to be stable to freeze-thaw cycling, stable to thermal cycling stress, and stable to mechanical stress, and stable to hydrolysis under steam sterilization conditions. It is anticipated that after thermal sterilization, the preferred compositions of this invention will be stable during a storage time prior to administration. The storage time can be relatively short, i.e., a composition can be used immediately after cooling to a temperature suitable for administration such as from about 5° C. to about 37° C. Preferably however, the storage time is relatively long, i.e., a composition can be sterilized and then cooled to a suitable storage temperature such as from about 5° C. or less to about room temperature such as from about 15° C. to about 25° C., for a storage time ranging up to at least one month, preferably up to at least six months, more preferably up to at least one year, and most preferably up at least 2 years or more. Alternatively, a composition of this invention can be sterilized and then frozen during a first storage time such as any of those outlined above, then thawed and used during a second storage time above the freezing point of the composition prior to administration where the second storage time is at least one hour, preferably at least one day, more preferably at least one week, even more preferably at least one month, even more preferably at least six months, yet even more preferably at least one year, and most preferably at least two years.

3. Administration of the Intravenous Formulations

The present invention also provides a method for treating patients suffering from abnormal cell proliferation such as cancer by using the pharmaceutical composition described above.

The pharmaceutical compositions of the present invention, prior to administration, may be further diluted as desired by adding an aqueous solution, such as water, saline or other infusion fluid, and used for intravenous injection or infusion. For example, the pharmaceutical composition can be diluted with sterile water, normal saline, D5W, Ringer's solution or other equivalent infusion liquids. Dilution of the composition preferably ranges from 1:10 to 1:500 v/v of the composition to the diluting infusion liquids. The dilution may also be appropriately adjusted according to the specific treatment schemes adopted by clinicians. The ratio of v/v in this context refers to the ratio of the volume of the composition before dilution with the infusion fluids to the total volume of the pharmaceutical formulation following dilution with the infusion fluid.

Prior to administration, the compositions of the present invention may contain varying amounts of a camptothecin compound. In a preferred embodiment, the concentration of the camptothecin compound in the composition is greater or equal to about 1.0 mg/ml, and more preferably greater or equal to about 2 mg/ml.

4. Indications for Treatment with the Composition of the Present Invention

Preferable indications that may be treated using the compositions of the present invention include those involving undesirable or uncontrolled cell proliferation. Such indications include benign tumors, various types of cancers such as primary tumors and tumor metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. It is noted, however, that the formulations of the present invention may be used to intraveneously or intrathecally deliver camptothecin for any indication for which camptothecin is useful.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fingoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrom), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanim of various angiogenic factors, including elements of the inflammatory response, such as leukocytes, platelets, cytokines, and eicosanoids, or unidentified plasma constituents have yet to be revealed.

In another embodiment of the present invention, a method is provided for treating diseases associated with undesired and uncontrolled angiogenesis. The method comprises administering to a patient suffering from uncontrolled angiogenesis the pharmaceutical composition of the present invention. The particular dosage of the camptothecin compound requires to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the composition of the present invention may be used to treat a variety of diseases associated with uncontrolled angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment of the present invention, a method is provided for treating chronic inflammatory diseases associated with uncontrolled angiogenesis. The method comprises administering to a patient suffering from a chronic inflammatory disease associated with uncontrolled angiogenesis the pharmaceutical composition of the present invention. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the composition of the present invention may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rhematoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the composition of the present invention should inhibit the formation of the sprouts and prevent the formation of granulomas. The inflammatory bowel diseases also exhibit extra intestinal manifectations, such as skin lesions. Such lesions are characterized by inflammation and angiogenesis and can occur at many sites other the gastrointestinal tract. Inhibition of angiogenesis by the composition of the present invention should reduce the influx of inflammatory cells and prevent the lesion formation.

Sarcoidois, another chronic inflammatory disease, is characterized as a multisystem granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the composition of the present invention to inhibit angionesis, such granulomas formation can be inhibited. Psoriasis, also a chronic and recurrent inflammatory disease, is characterized by papules and plaques of various sizes. Treatment using the composition of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the composition of the present invention alone or in conjunction with other anti-RA agents should prevent the formation of new blood vessels necessary to maintain the chronic inflammation and provide the RA patient relief from the symptoms.

In a preferred embodiment, this invention comprises a method of treatment of neoplastic cells or rapidly proliferating cells in a patient comprising administering by intravenous injection a therapeutically effective amount of an injectable pharmaceutical composition comprising a dispersion of micrometer to submicrometer size solid particles in an aqueous carrier solution of one or more pharmaceutically acceptable tonicity modifier agents, the particles comprising:

a camptothecin drug, a first coating of not more than 10% w/w of a substantially water-insoluble, pharmaceutically acceptable lipophilic agent in which the camptothecin drug is insoluble or poorly soluble, and a second coating of at least one membrane-forming surface stabilizing amphipathic lipid, wherein the dispersion does not aggregate, flocculate, or agglomerate, and the particles do not grow in size above a volume weighted mean diameter of 10 μm upon steam sterilization and storage prior to administration to a patient.

In another preferred embodiment, this invention comprises a method of treatment of neoplastic cells or rapidly proliferating cells in a patient comprising administering by intravenous injection a therapeutically effective amount of an injectable pharmaceutical composition comprising a dispersion of micrometer to submicrometer size solid particles in an aqueous carrier solution of one or more pharmaceutically acceptable tonicity modifier agents, the particles comprising:

a camptothecin drug, and a coating of at least one membrane-forming surface stabilizing amphipathic lipid, wherein the dispersion does not aggregate, flocculate, or agglomerate, and the particles do not grow in size above a volume weighted mean diameter of 10 μm upon steam sterilization and storage prior to administration to a patient.

In another preferred embodiment, this invention comprises a method of treatment of neoplastic cells or rapidly proliferating cells in a patient comprising administering by intravenous injection a therapeutically effective amount of an injectable pharmaceutical composition comprising a dispersion in an aqueous carrier solution of one or more pharmaceutically acceptable tonicity modifier agents of micrometer to submicrometer size spherical liquid droplets of a substantially water-insoluble, pharmaceutically acceptable lipophilic liquid vehicle containing in a dissolved form a camptothecin drug and at least one membrane-forming amphipathic lipid, the liquid droplets being surrounded by a layer comprising at least one membrane-forming amphipathic lipid, wherein upon steam sterilization and storage prior to administration to a patient, the dispersion does not aggregate, flocculate, agglomerate, or coalesce, and the droplets do not grow in size above a volume weighted mean diameter of 10 μm.

In another preferred embodiment, this invention comprises a method of treatment of neoplastic cells or rapidly proliferating cells in a patient comprising administering by intravenous injection a therapeutically effective amount of an injectable pharmaceutical composition comprising an aqueous carrier solution of one or more pharmaceutically acceptable tonicity modifier agents, said solution containing a dispersion of spherical liquid droplets of a first size distribution of a substantially water-insoluble, pharmaceutically acceptable lipophilic liquid vehicle, said vehicle containing solid particles of a camptothecin drug of a second size distribution together with the camptothecin drug in a dissolved form and at least one membrane-forming amphipathic lipid, the liquid droplets being surrounded by a layer comprising at least one membrane-forming amphipathic lipid, wherein the first size distribution is in the range of submicrometer to micrometers, and the second size distribution is smaller than the first size distribution, and wherein upon autoclave sterilization and storage prior to administration to a patient, the dispersion does not aggregate, flocculate, agglomerate, or coalesce, and the droplets do not grow in size above a volume weighted mean diameter of 10 μm.

In another preferred embodiment, this invention comprises a method for administering a camptothecin to a patient comprising intravenously administering to a patient a pharmaceutical composition suitable for intravenous administration to a mammal comprising an aqueous suspension of particles having mean diameters between about 0.05 μm and 10 μm, the particles comprising a core containing a camptothecin compound having an intact lactone ring, wherein the core of each particle is stabilized against an increase in particle size of more than 100% during a sterilization step and during a storage time by a membrane-forming amphipathic lipid coating on the surface of the core and by one or more tonicity modifying agents, wherein the ratio of lipid to the camptothecin compound is less than about 150:1 moles:mole, and wherein the coating substantially protects the lactone ring of the camptothecin compound from interaction with water to prevent hydrolysis during formation of the particle, during sterilization of the particle in the suspension, and during storage of the particle in the suspension prior to administration.

In another preferred embodiment, this invention comprises a method for administering a camptothecin to a patient comprising intravenously administering to a patient a pharmaceutical composition suitable for intravenous administration to a mammal comprising an aqueous suspension of particles having mean diameters between about 0.05 μm and 10 μm, the particles comprising a solid core containing a camptothecin compound having an intact lactone ring, wherein the core of each particle is stabilized against an increase in particle size of more than 100% during a sterilization step and during a storage time by a membrane-forming amphipathic lipid coating on the surface of the core and by one or more tonicity modifying agents, wherein the ratio of lipid to the camptothecin compound is less than about 150:1 moles:mole, and wherein the coating substantially protects the lactone ring of the camptothecin compound from interaction with water to prevent hydrolysis during formation of the particle, during sterilization of the particle in the suspension, and during storage of the particle in the suspension prior to administration.

In another preferred embodiment, this invention comprises a method for administering a camptothecin to a patient comprising intravenously administering to a patient a pharmaceutical composition suitable for intravenous administration to a mammal comprising an aqueous suspension of particles having mean diameters between about 0.05 μm and 10 μm, the particles comprising a solid core of a camptothecin compound having an intact lactone ring, wherein the core of each particle is stabilized against an increase in particle size of more than 100% during a sterilization step and during a storage time by a membrane-forming amphipathic lipid coating on the surface of the core and by one or more tonicity modifying agents, wherein the ratio of lipid to the camptothecin compound is less than about 150:1 moles:mole, and wherein the coating substantially protects the lactone ring of the camptothecin compound from interaction with water to prevent hydrolysis during formation of the particle, during sterilization of the particle in the suspension, and during storage of the particle in the suspension prior to administration.

In another preferred embodiment, this invention comprises a method for administering a camptothecin to a patient comprising intravenously administering to a patient a pharmaceutical composition suitable for intravenous administration to a mammal comprising an aqueous suspension of particles having mean diameters between about 0.05 μm and 10 μm, the particles comprising a core containing a camptothecin compound having an intact lactone ring, wherein the core of each particle is a liquid stabilized against an increase in particle size of more than 100% during a sterilization step and during a storage time by a membrane-forming amphiphatic lipid coating on the surface of the core and by one or more tonicity modifying agents, wherein the ratio of lipid to the camptothecin compound is less than about 150:1 moles:mole, and wherein the coating substantially protects the lactone ring of the camptothecin compound from interaction with water to prevent hydrolysis during formation of the particle, during sterilization of the particle in the suspension, and during storage of the particle in the suspension prior to administration.

EXAMPLES

The following examples set forth methods of preparing compositions according to the present invention, studies regarding their stability, as well as studies regarding their tumor growth suppression for different cancer types, specifically melanoma, breast cancer, lung cancer, and pancreatic cancer. In each study, a high level of tumor growth suppression was achieved using a formulation according to the present invention.

1. Phospholipid Stabilized Solid Particulate Dispersion of 9-Nitro-Camptothecin of Micrometer to Submicrometer Dimensions In order to illustrate how one might prepare micrometer to submicrometer size particle dispersions of 9-nitro-camptothecin in aqueous injectable medium according to the present invention, the following example describes the preparation of several such dispersions. One of the dispersions described herein (formulation 1-F, also referred to as IDD-P) was employed in the various tumor growth suppression studies described herein.

Aqueous dispersions of micrometer to submicrometer size particles of 9-nitro-camptothecin containing the ingredients and amounts listed in FIG. 1 were prepared by adding a phospholipid and 9-nitro-camptothecin to an aqueous solution containing the remaining ingredients and stirring the mixture under high shear to form a pre-mix dispersion under a nitrogen atmosphere. The pH of the premix was adjusted with 1N NaOH or 20% acetic acid to about 5.5. The acidification of the premix was performed in order to prevent hydrolysis of the α-hydroxy lactone ring of 9-nitro-camptothecin.

The pre-mix dispersion was then subjected to high pressure homogenization under nitrogen at pressures in the range of 10,000 psi to 25,000 psi for a number of volume passes sufficient to achieve the desired particle size distribution by recirculating the process fluid through an Avestin Emulsiflex C5 homogenizer, Avestin Inc., ON, Canada. One volume pass is equal to the volume of the starting process fluid that is pumped through the homogenizer's size reduction valve. The material exiting the size reduction valve is continuously recirculated to the homogenizer's inlet reservoir for reprocessing. During the homogenization and particle size reduction process, the process fluid was cooled by passing through a heat exchanger set to approximately 10° C. to maintain the dispersion at a temperature below 45° C. at the exit of the size reduction valve and elsewhere in the process fluid loop.

The homogenized process fluid was then collected in a clean vessel at ambient temperature under nitrogen atmosphere, and diluted with an aqueous solution containing pH buffering agents (sodium acetate and acetic acid) and tonicity modifier (either mannitol or trehalose) to give a final concentration of sodium acetate of 2 mM, and that of the other ingredients shown in FIG. 1.

FIG. 1 also summarizes representative sample compositions and observations. For example, the amounts of 9-nitro-camptothecin (9NCA), phospholipid (Lipoid E80; employed as a surface modifier), and polyhydroxy compounds (mannitol (MAN) and trehalose (TRE); useful as tonicity modifying agents) are shown in the figure. Representative physical attributes such as particle sizes of the formulations are also shown in the figure.

The pH of the diluted product was measured and adjusted to 5.5 as necessary. The product was then filled into borosilicate USP Type I glass vials. These vials were sealed under a nitrogen atmosphere with PTFE gray butyl stoppers and subjected to terminal steam sterilization at 121° C. for 15 to 30 minutes. The volume-weighted diameters of the resulting suspensions, also reported in FIG. 1, were determined with a Malvern Mastersizer Microplus apparatus which utilizes a method based on diffraction of light by the particulate suspension to provide a measure of particle size.

The steam sterilized suspensions were found to have particle size distributions that contained no particles greater than 7 μm. Suspensions of particles in this size range are considered acceptable for intravenous injection into mammals, including human subjects. Formulations of identification 1-A, 1-B, and 1-C contain mannitol that modifies the osmotic pressure of the suspensions to provide osmolalities of the suspensions suitable for intravenous injection. A suitable osmolality is one for example that is substantially isotonic with blood. Formulations of identification 1-D, 1-Ea, 1-Eb, 1-Ec, 1-F and 1-V contain trehalose as the osmotic pressure modifier. These suspensions can be diluted for example with water for injection or other suitable sterile aqueous solution with low osmolality to render them isotonic with blood and suitable for intravenous injection.

The formulation identified as 1-V does not contain any active drug and may be used as a placebo. This formulation can also be used as a diluent for the formulations containing the active drug in dose ranging studies.

A. Stability of Sterile Suspensions of 9-nitro-camptothecin Particles Under Freeze-thaw Stress The formulation identified as 1-F in FIG. 1 was used in the following freeze/thaw stress experiment. This same formulation is identified as IDD-P herein and was used in the below described tumor growth suppression studies.

A subset of vials containing the 1-F formulation was cooled in a freezer to approximately −20° C. for at least 6 hours to freeze the suspensions contained therein. The frozen samples were then thawed by placing the vials at room temperature for 0.5–1 hour. Particle size distribution of one of the thawed samples was measured by the method mentioned above, and the appearance of the thawed sample was recorded. The remaining sample contained in the opened vial used for these measurements was then discarded. The remaining vials of this set were used for repeated freeze/thaw cycles similar to the above.

The formulation 1-F displayed very good particle size stability under the stress of repeated freeze/thaw conditions. For example, the initial volume weighted mean particle diameter of this formulation was 1.29 μm and 99.9% of the particles were of a size less than 2.8 μm. Even after three cycles of the above freeze/thaw stress conditions, the volume weighted mean particle diameter remained substantially unchanged at 1.28 µm and 99.9% of the particles were of a size less than 2.99 µm, substantially unchanged from the original measurement. This experiment demonstrates the robustness of the formulation against the freeze/thaw stress.

B. Stability of Sterile Suspensions of 9-nitro-camptothecin Particles Under Thermal Cycling Stress The formulation identified as 1-F in FIG. 1 was also used in the following thermal cycling stress experiment. In this experiment, a thermal cycling stress sequence was applied to a subset of vials containing the 1-F formulation by storing the set for approximately 24 hours in a refrigerator at about 4° C. and then in an incubator at about 40° C. for approximately 24 hours. The refrigeration/warming cycle was then repeated for three cycles. The particle size of a thermally stressed suspension was measured and its appearance noted at the end of each cycle. After each particle size measurement, the vial used for measurement was discarded.

The suspensions demonstrated very good particle size distribution stability and appearance after three cycles of thermal cycling stress. After three thermal cycles the volume weighted mean particle diameter of this formulation was substantially unchanged, increasing from an initial value of 1.29 µm to only 1.33 µm. In addition, 99.9% of the particles remained below a size less than 3.44 µm after three thermal cycles. This demonstrates the robustness of the formulation against the thermal cycling stress generated by repeated transfer or cycling of the formulation between 4° C. and 40° C.

C. Stability of Sterile Suspensions of 9-nitro-camptothecin Particles Under Shaking-standing Stress The formulation identified as 1-F in FIG. 1 was also used in the following shaking-standing stress experiment. In this example, a subset of vials containing the 1-F formulation was placed on an orbital shaker with each vial of the set being horizontal. The vials were shaken at approximately 100 rpm. One vial was removed from the shaker daily for observation of the appearance of the suspension and for particle size measurement. The volume weighted mean particle size distribution and the 99.9 percentile size of the suspension did not change significantly on shaking for up to 3 days after which the study was terminated. After three days of shaking the volume weighted mean particle size remained 1.28 µm and its 99.9 percentile remained under 3.02 µm.

D. Stability of Sterile Suspensions of 9-nitro-camptothecin Particles Under Different Temperatures for 170 Days The formulation identified as 1-F in FIG. 1 was also used in the following temperature stability experiment. Three sets of vials containing the sterilized formulation were placed in incubators held at 4° C., 25° C., and 40° C. A vial was removed from the incubator for observation of the appearance and particle sizing. FIG. 2 summarizes the volume weighted mean particle size and 99.9 percentile data for the temperature stability study. The volume weighted mean particle size of the suspensions did not change significantly on storage for up to 170 days on storage at 4° C., 25° C., and 40° C. The 99.9 percentile size did not substantially change on storage for up to 170 days on storage at 4° C. and 25° C.

2. Method for Preparing Droplet Suspension of 9-Nitro-camptothecin

In order to illustrate how to prepare phospholipid droplet suspensions of 9-nitro-camptothecin according to the present invention, the following example describes the preparation of a formulation of 9-nitro-camptothecin referred to herein as "IDD-D". The IDD-D formulation is employed in the various tumor growth suppression studies described herein.

First, an oil phase was prepared by dissolving 0.4 g of 9-nitro-camptothecin, 40.0 g of Lipoid EPC (purified egg phosphatidyl choline, Lipoid GmbH, Ludwigshafen Germany), 20.0 g of cholesterol (Sigma, St. Louis, Mo.), and 4.0 g of dimyristoylphosphatidyl glycerol (Avanti Polar Lipids, Alabaster, Ala.) in a mixture of 200 g of a medium chain triglyceride (Crodamol GTCC PN, Caprylic/Capric Triglyceride, Croda Inc., Parsippany, N.J.) and 200 g of soybean oil (Spectrum Quality Products Inc., New Brunswick, N.J.) with magnetic stirring. After complete dissolution of all components, the solution was stirred for an additional 10 min. A water phase was prepared by dissolving 80.0 g of mannitol (J. T. Baker, Phillipsburg, N.J.) in 1455.6 g of water and the solution was then purged with nitrogen.

An IDD-D premix comprising a mixture of the two solutions was prepared by transferring the oil phase under nitrogen pressure into the water-phase and dispersing the mixture by rapid stirring under a nitrogen cover. Sufficient quantity of 1N NaOH or 20% acetic acid was added to adjust the pH to 7.5.

The premix was homogenized at 7,000–8,000 psig using a Microfluidizer 110S (Microfluidics, Newton, Mass.) under a nitrogen cover. The product was recirculated into the Microfluidizer via a heat exchanger cooled with a chiller set at 15–20° C. The homogenized product was collected and filled into 10 mL USP Type I borosilicate clear glass vials under a nitrogen atmosphere using 10.2–10.5 g of product per vial. A TEFLON® faced gray butyl stopper was applied to each vial which was then further sealed with an aluminum flip-off seal. The sealed vials and their contents were steam sterilized by autoclaving at 121° C. for 20 min with the vials maintained in a vertical position, and then quench-cooled with about 10–15° C. water for 10 min. The steam sterilized product was characterized by pH determination and particle sizing (Nicomp 370; Particle Sizing Systems Inc., Santa Barbara, Calif. This equipment uses quasi-elastic laser light scattering for particle size determination). The volume weighted particle size of the steam sterilized product, referred to herein as IDD-D, was 0.2 µm, and 99.9 percent of the particle population was smaller than about 0.34 µm. The suspension had a pH of 7.0 after steam sterilization.

D. Stability of 9-nitro-camptothecin Suspension in IDD-D

The suspension formed according to this example was used for evaluating stability against the stress conditions detailed in the previous examples, namely, storage at 2–8° C., 20° C., and 40° C., thermal cycling between 4° C. and 40° C., and shaking at ambient temperature. FIG. 3 summarizes the particle size stability data from these stability studies. Overall, the formulation displayed very good particle size stability under the different potentially destabilizing stress conditions.

3. Melanoma Xenograft Model Study 1

The following study evaluates two intravenous formulations according to the present invention against human tumor xenografts in athymic nude mice. The study used the A375 human melanoma xenograft model to compare the in vivo antitumor efficacy of I.V. 9-nitro-camptothecin, in vehicles containing IDD-P which provides a particulate suspension of 9-nitro-camptothecin, and IDD-D which provides a droplet suspension of 9-nitro-camptothecin, to the efficacy of oral 9-nitro-camptothecin and intraperitoneal CAMPTOSAR®, HYCAMTIN®, and DTIC®. Examples 1 and 2 describe the compositions of IDD-P (FIG. 1; formulation 1-F) and IDD-D respectively.

In order to assess antitumor efficacy, groups of athymic nude mice (n=10) bearing ~72-mg A375 melanomas were treated intravenously on the 5/2/5 schedule with 9-nitrocamptothecin in IDD-P at 3.0 mg/kg or 1.5 mg/kg and 9-nitro-camptothecin in IDD-D at 2.0 mg/kg or 1.0 mg/kg.

The 3.0 mg/kg doses of 9-nitro-camptothecin in IDD-P produced five 62-day survivors, including one complete regression (CR) and three partial regression (PR) responses. It is noted that a high 30% toxic death rate was observed.

The 1.5 mg/kg doses of 9-nitro-camptothecin in IDD-P produced two CR and 1 SD/PD responses, no toxic deaths, and a mean day of survival (MDS) of 50.7 days (n=7), compared to the MDS of 29.2 days for the vehicle control group (n=10).

9-nitro-camptothecin in IDD-D at 2 mg/kg produced two survivors and an MDS of 47.2 days. The 1.0 mg/kg doses had no significant activity.

Treatment with 1.5 mg/kg 9-nitro-camptothecin in IDD-P was superior to I.P. CAMPTOSAR® (100 mg/kg, qwk×3), HYCAMTIN® (10 mg/kg, q4d×4), and DTIC® (150 mg/kg, qd×5). Each of the latter treatments produced a single CR response and MDS values of 47.3, 46.7, and 37.6 days, respectively. 9-nitro-camptothecin in IDD-P appeared less effective than oral 9-nitro-camptothecin in 3% DMA (4.0 or 2.0 mg/kg, Days 1, 4, 8, 11), which gave seven survivors, including four CR responses, and MDS values of 45.3 and 47.6 days, respectively.

In summary, IDD-P and IDD-D were well tolerated as I.V. vehicles. The anti-melanoma activity of I.V. 9-nitro-camptothecin appeared to be greater in a vehicle containing IDD-P than one with IDD-D. Therapy with 1.5 mg/kg 9-nitro-camptothecin in IDD-P was highly effective and appeared superior to optimal I.P. treatments with CAMPTOSAR®, HYCAMTIN®, or DTIC®. 9-nitro-camptothecin in IDD-P appeared less effective at 1.5 mg/kg on the 5/2/5 schedule than oral 9-nitro-camptothecin in 3% DMA at 2 mg/kg on a q3d×4 schedule, which produced more survivors. The MTD of I.V. 9-nitro-camptothecin in IDD-P is >2 mg/kg and <3 mg/kg on a 5/2/5 schedule.

A. Methods and Materials

Abbreviations

The following table summarizes the abbreviations used to describe this study.

Abbreviations

| | |
|---|---|
| CR | complete tumor regression, tumor not detected at termination of the study on Day 62 |
| DMA | N,N-dimethylacetamide |
| D5W | Dextrose 5% in water, pH @ 4.8 |
| I.P. | intraperitoneal |
| I.V. | intravenous |
| MTD | maximum tolerated dose; dose associated with no more than one death among ten treated mice and less than 20% mean body-weight loss |
| p.o. | per os, oral |
| PR | partial tumor regression, tumor weight on Day 62 lower than on Day 1 |
| qd × 5 | 1 dose per day for 5 days (Days 1–5) |
| q3d × 4 | 4 doses delivered as one dose per day at 3-day intervals |
| q4d × 4 | 4 doses delivered as one dose per day at 4-day intervals |
| qwk × 3 | one dose per week for three weeks (Days 1, 8, 15) |
| SD/PD | survival to 62 days with a stable or progressively increasing tumor weight |
| TGD | tumor growth delay, MDS treated - MDS control, the extension of survival time |

Husbandry

Female nude mice were 16 weeks of age (NCR-nuJBr; Taconic Farms) for the A375 study. The mice were fed ad libitum water (reverse osmosis, 1 ppm Cl) and autoclaved Prolab NIH-31 M/5% Rodent Diet consisting of 18% protein, 5% fat, 6% fiber, and 8% ash. Mice were housed in static microisolators on a 12-hour light cycle at 21–22° C. (70–72° F.) and 40%–60% humidity. The animal care and use program is AAALAC International accredited and specifically follows and complies with the recommendation of the National Research Council's *Guide for the Care and Use of Laboratory Animals*.

Tumor Implantation

An A375 melanoma fragment (1 mm 3) was implanted subcutaneously in the flank of each nude mouse. When the tumors reached the 60–112 mg size range, the mice were sorted into treatment groups (on Day 1) such that the group mean tumor sizes ranged from 71.3 mg–72.5 mg. Estimated tumor weight was calculated using the formula:

$$\text{Tumor Weight (mg)} = \frac{w^2 \times l}{2}$$

where w=width and l=length in mm of an A375 melanoma.

Drug Formulations

IDD-P with a mean particle size of 0.07–0.06 mm and IDD-D with a mean particle size of 0.15 mm were prepared for the study by RTP Pharma Inc. For this, the 9-nitro-camptothecin suspensions were diluted with water and vehicle to provide doses of 3 mg/kg and 1.5 mg/kg in 33% IDD-P, and doses of 2 mg/kg and 1 mg/kg in 100% and 50% IDD-D, respectively. After dilution, 9-nitro-camptothecin suspensions were mixed thoroughly by gentle agitation and stored at 2–8° C. For its oral formulation, 9-nitro-camptothecin was dissolved in DMA (N,N-dimethylacetamide, SIGMA) and diluted with D5W to yield a final DMA concentration of 3%. CAMPTOSAR®, DTIC®, and HYCAMTIN® were obtained as the marketed drugs and solutions were prepared fresh on the day of dosing. CAMPTOSAR® (irinotecan, Pharmacia & Upjohn Company, 20 mg/ml) and DTIC® (dacarbazine, Bayer Corporation, 20 mg/ml) were diluted with D5W. HYCAMTIN® (topotecan, SmithKlein Beecham) was reconstituted with water at 1 mg/ml.

Treatments

Volumes of 0.20 ml per 20-g mouse, body-weight adjusted, were administered once daily. Tumor-bearing athymic nude mice were matched on Day 1 into 13 groups of ten animals and drug administration was initiated. The I.V. formulations of 9-nitro-camptothecin were given once daily on a 5/2/5 schedule as shown in the protocol summary shown in FIG. 4. Oral 9-nitro-camptothecin doses were given on a q3d×4 schedule (Days 1, 4, 8, and 11). Three reference drugs were administered I.P.: CAMPTOSAR® was given in three doses at weekly intervals (qwk×3); HYCAMTIN® was given in four doses at four-day intervals (q4d×4); and DTIC® was given in five consecutive daily doses (qd×5). The tumor growth control group for these reference treatments received no treatment (Group 1). The 9-nitro-camptothecin vehicle: 33.3% IDD-P, 100% IDD-D, and 3% DMA, was administered to vehicle control Groups 2–4, respectively.

Tumor Growth Endpoint

The tumor growth delay (TGD) method was used to assess efficacy. Tumor dimensions were measured twice weekly until the experiment was terminated on Day 62. Each animal was euthanized as a "cancer death" when its A375 melanoma reached a size of 2.0 g. Mean Day of Survival (MDS) values for all groups were based on the calculated day of death of each mouse, which is given by the formula:

$$\text{Time to endpoint (calculated)} =$$

$$\text{Time to exceed endpoint (observed)} - \frac{Wt_2 - \text{endpoint weight}}{\frac{Wt_2 - Wt_1}{D_2 - D_1}}$$

where:
Time to exceed endpoint (observed)=number of days it takes for each tumor to grow past the endpoint (cut-off) size. This is the day the animal is euthanized as a cancer death.
$D_2$=day animal is euthanized.
$D_1$=last day of caliper measurement before tumor reaches the endpoint.
$Wt_2$=tumor weight (mg) on $D_2$
$Wt_1$=tumor weight (mg) on $D_1$
Endpoint weight=predetermined "cut-off" tumor size for the model being used.

TGD values, which represent treatment-effected extensions of survival time, were calculated from $\text{MDS}_{treated} - \text{MDS}_{control}$, the difference in MDS value for a given treatment group and the MDS value for A375 melanoma-bearing mice that received no treatment or the corresponding vehicle.

At the termination of the experiment on Day 62, treatment responses in survivors were classified as either complete tumor regression (CR), partial tumor regression (PR), or stable/progressive disease (SD/PD). A CR response indicates the absence of measurable tumor. In a PR response, the final tumor weight is lower than on Day 1 but larger than 0 mg. In a SD/PD response, mice survived to Day 62 with a progressively growing or stable tumor size that had not reached the 2.0-g endpoint.

Evaluation of Toxicity

The maximum tolerated dose (MTD), as defined by the NCI, is the highest dose at which no more than 10% of the animals die and the group mean body-weight loss is no more than 20%. Body weights were measured daily for four or five days and then twice weekly thereafter until the experiments were terminated on Day 62 of the study. The animals were also examined frequently for clinical signs of any adverse, drug-related side effects. Because mice are not tagged for MTD studies, only the mean group body weights recorded in the appended raw data are significant in those studies.

Statistics

The unpaired t-test and Mann-Whitney U test (analyzing means and medians, respectively) were employed to determine the statistical significance of any difference in MDS between a treatment group and the control group, and between different treatment groups. Kaplan-Meier plots were constructed and the log-rank test was used to evaluate the differences in the effects of treatments on TGD outcome. All analyses for statistical significance were conducted at P level of 0.05 (two-tailed). Prism (GraphPad) version 3 was used for the statistical analyses and graphic presentations.

B. Results

The protocols for 13 groups of A375 tumor-bearing mice (n=10) are shown in FIG. 4. The therapeutic and toxic responses for all groups are summarized in FIG. 5. The individual survival times for the mice in all groups are presented as a scatter plot in FIG. 6.

Tumor Growth in the Control Mice

The A375 melanomas in untreated mice (Group 1) reached the 2.0-g endpoint in nine animals to give a mean day of survival (MDS) of 30.3±4.4 days. The one 62-day survivor with apparently stable/progressive disease (SD/PD) may be taken to represent the background level for somewhat poor tumor takes. The MDS values for vehicle control mice (Groups 2–4) treated I.V. with 33.3% IDD-P, 100% IDD-D, and 3% DMA, respectively, were similar to the MDS of the untreated control (FIG. 5). The apparent complete remission (CR) response of one mouse in Group 4 may represent a poor tumor take. FIG. 6 shows that the survival times of the untreated mice in Group 1 are more widely scattered than those of the vehicle control mice, Groups 2–4.

Therapeutic Effects of Intraperitoneal CAMPTOSAR®, HYCAMTIN®, and DTIC®

To provide reference standards for the 9-nitro-camptothecin treatments, three groups of mice were treated I.P. with a camptothecin analog, CAMPTOSAR® or HYCAMTIN®, or with an alkylator, DTIC®, using the optimal regimen for each drug. The untreated mice in Group 1 were used as the controls for these reference therapies. Treatment of Group 5 with CAMPTOSAR® at 100 mg/kg qwk×3 produced an MDS of 47.3 days (n=9) and one survivor with a CR response. The tumor growth delay (TGD) of 17 days was statistically significant (P value of 0.0038, unpaired two-tailed t-test). Treatment of Group 6 with HYCAMTIN® at 10 mg/kg q4d×4 gave an MDS of 46.7 days (n=9), for a statistically significant TGD of 16.4 days (P value of 0.006, t-test). There was one survivor with a CR response. Treatment of Group 7 with DTIC® at 150 mg/kg qd×5 produced an MDS of 37.6 days (n=8), one CR response, and one toxic death. The TGD of 7.3 days was not statistically significant (P value of 0.248, t-test). Given the one SD/PD response in the untreated control and the one CR response in the 3% DMA vehicle control group, it is uncertain whether these single CR responses in Groups 5–7 can be attributed to treatment efficacy.

Efficacy of I.V. 9-nitro-camptothecin in IDD-P

The I.V. 9-nitro-camptothecin treatments were all administered on a 5/2/5 schedule (Days 1–5 and 8–12). Group 2 mice, with an MDS of 29.2±2.5 days (FIG. 3), served as the vehicle control. Ten doses of 3.0 mg/kg 9-nitro-camptothecin in IDD-P proved both highly effective and highly toxic in Group 8 mice. The MDS of 52 days (n=2) gave a significant TGD of 22.8 days (P value of 0.0027, t-test). There was a 50% survival rate and a 30% toxic death rate. There were 1 CR, 3 partial remission (PR), and 1 SD/PD responses recorded on Day 62. The calculated mean tumor weight for Group 8 remained below the Day 1 level until Day 34. This was the longest transient PR response recorded for any group in this study.

Figure 7:
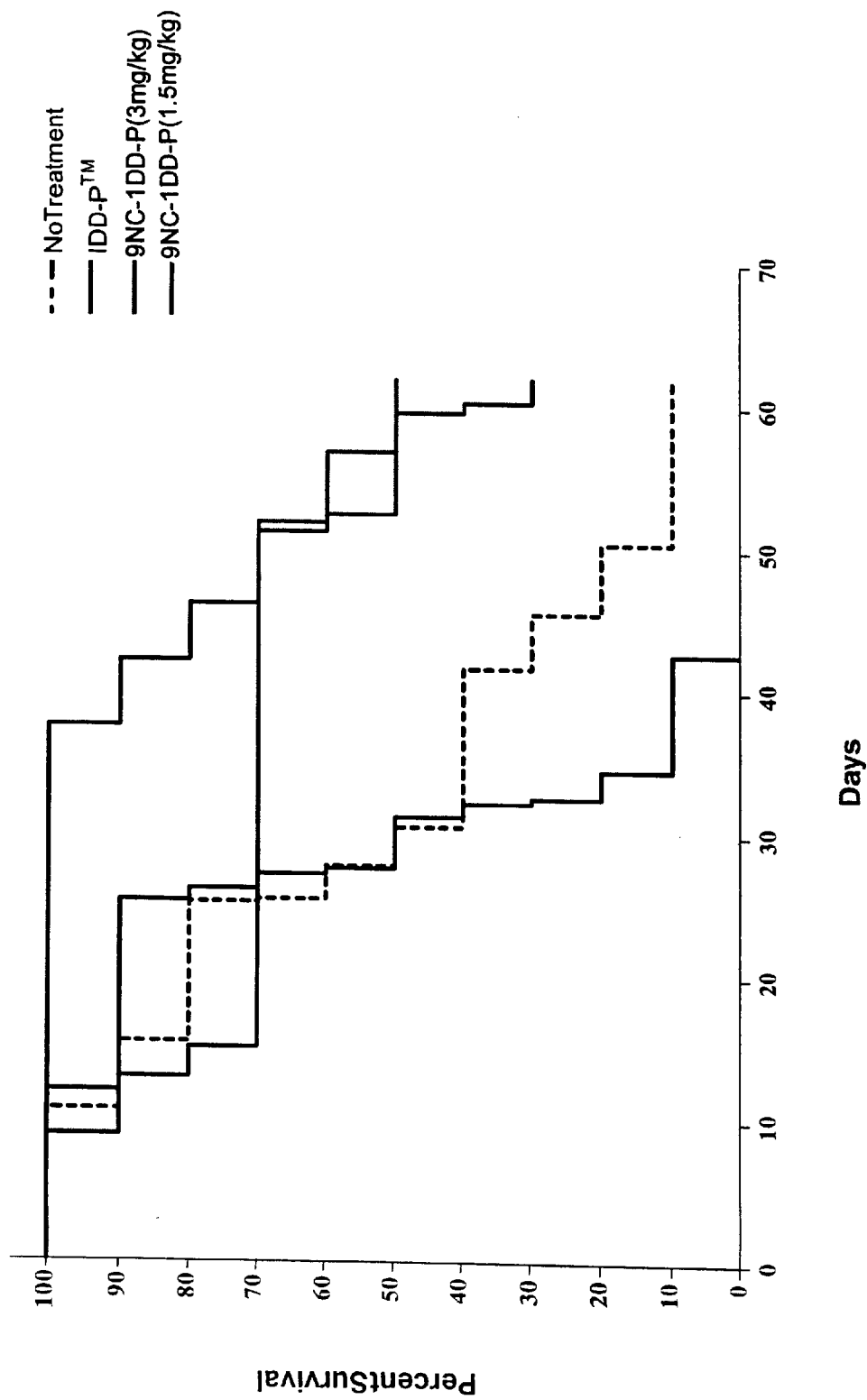
FIG. 7 shows Kaplan-Meier survival curves from the first melanoma study for untreated mice and mice treated with 9-nitro-camptothecin in IDD-D or vehicle.

At the low dose of 1.5 mg/kg, 9-nitro-camptothecin in IDD-P was well tolerated by Group 9 mice. The MDS of 50.7 days (n=7) revealed a significant TGD of 21.5 days (P<0.0001, t-test). The 62-day survival rate was, however, reduced to 30% in Group 9. There were 2 CR and 1 SD/PD responses. The Kaplan-Meier survival curves for untreated mice and mice treated with 9-nitro-camptothecin in IDD-P or vehicle are shown in FIG. 7. When the MDS values for Groups 8 and 9 were compared by t-test analysis to the MDS for the untreated control, lower P values of 0.0555 and 0.0037 were obtained. This reflects the greater dispersion of survival times for Group 1 mice compared to survival times for Group 2.

Efficacy of I.V. 9-nitro-camptothecin in IDD-D

The I.V. treatments with 9-nitro-camptothecin in IDD-D at 2.0 mg/kg and 1.0 mg/kg produced MDS values of 47.2 days (n=8) and 32.6 days (n=10) in Groups 10 and 11, respectively. Group 3 with an MDS of 31.6±3.2 days served as the control. The 15.6-day TGD for the higher dose was statistically significant (P value of 0.005, t-test). Two 62-day survivors, 1 CR and 1 PR, were obtained with the 2.0 mg/kg dosing regimen; there were no survivors with the 1.0 mg/kg regimen. Kaplan-Meier survival curves for untreated mice and mice treated with 9-nitro-camptothecin in IDD-D or vehicle are presented in FIG. 8.

Efficacy of Oral 9-nitro-camptothecin in 3% DMA

Figure 8:
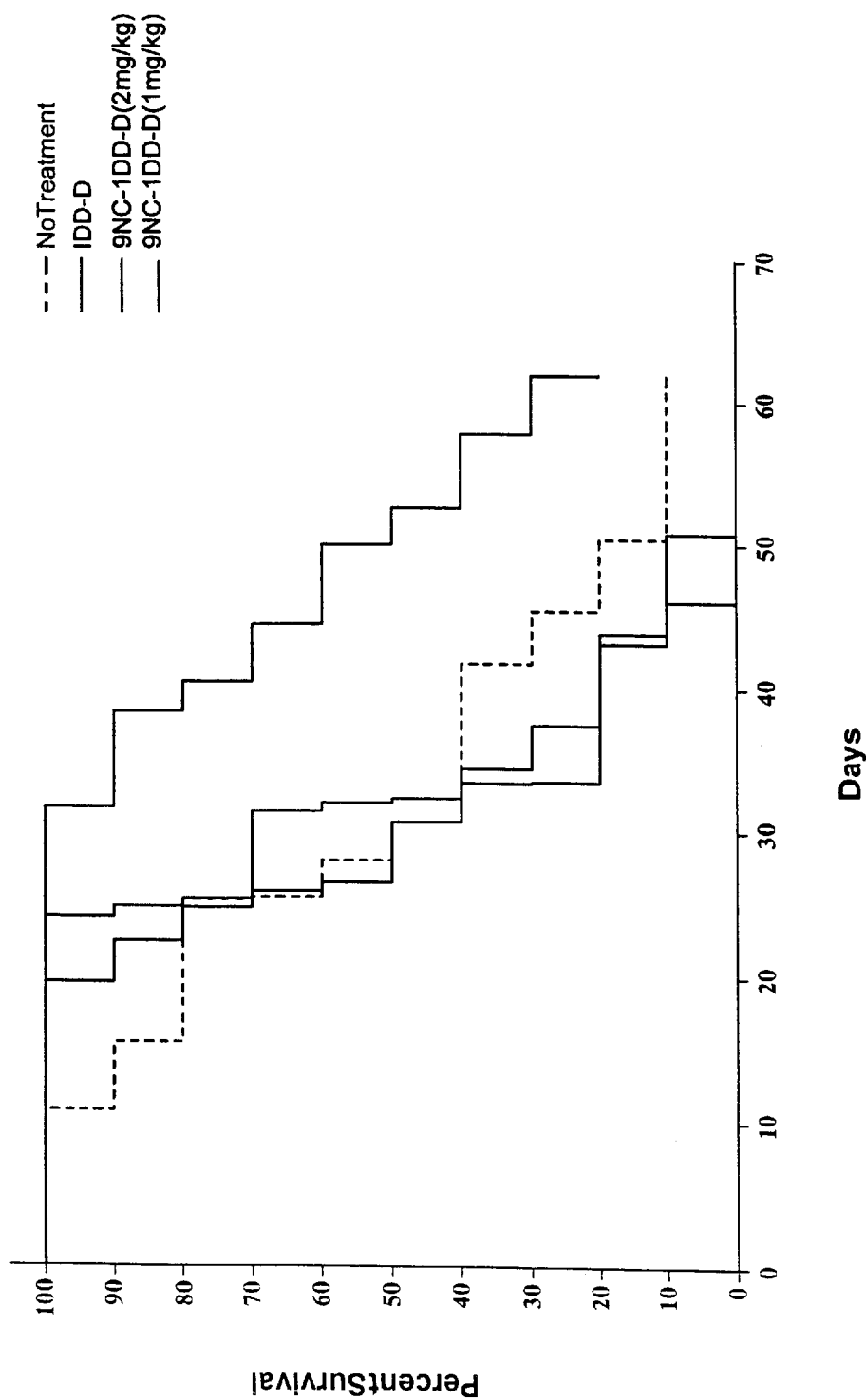
FIG. 8 shows the Kaplan-Meier survival curves from the first melanoma study for untreated mice and mice treated with oral 9-nitro-camptothecin in 3% DMA or vehicle.

The mice in Groups 12 and 13 were treated p.o. with 4.0 and 2.0 mg/kg 9-nitro-camptothecin in 3% DMA on a q3d×4 schedule (Days 1, 4, 8, and 11). Both therapies were well tolerated and produced 70% survival rates. There were 4 CR and 3 SD/PD responses at the higher dose and 4 CR, 1 RP, and 2 SD/PD responses at the lower dose. Group 4 with an MDS of 26.0±2.3 days served as the vehicle control. The MDS values of 45.3 days for Group 12 (n=3) and 47.6 days for Group 13 (n=3) provided significant TGDs of 19.3 days (P value of 0.0061, t-test) and 21.6 days (P value of 0.0007), respectively. FIG. 8 shows the Kaplan-Meier survival curves for untreated mice and mice treated with oral 9-nitro-camptothecin in 3% DMA or vehicle.

Toxicity in this Study

No toxicity was observed in any of the vehicle treatment groups. Three toxic deaths were recorded in Group 8 during or after treatment with 3.0 mg/kg 9-nitro-camptothecin in IDD-P on the 5/2/5 schedule. Two mice were found dead (Days 9 and 15) with bright pink lungs and impacted stomachs. There was evidence of diarrhea with one of the animals. A third mouse was euthanized for poor health on Day 13. This animal had bright pink lungs but an empty stomach and intestines. An acceptable group mean body weight loss of 13.1% was seen in Group 8 on Day 13. One toxic death was recorded on Day 13 in Group 7, which received DTIC®. This animal had lost 30% of its body weight by Day 5 and is responsible for most of the 5.2% mean group body-weight loss recorded for Group 7 on that day. Since none of the other mice showed significant body weight changes, this death may represent an event that is not drug related.

C. Discussion of Results

Intravenous administration of isotonic vehicles containing 33.3% IDD-P or 100% IDD-D was found to be well tolerated by athymic nude mice. The formulation of 9-nitro-camptothecin in these vehicles provided a highly efficacious I.V. treatment for mice bearing the human A375 melanoma.

Figure 9:
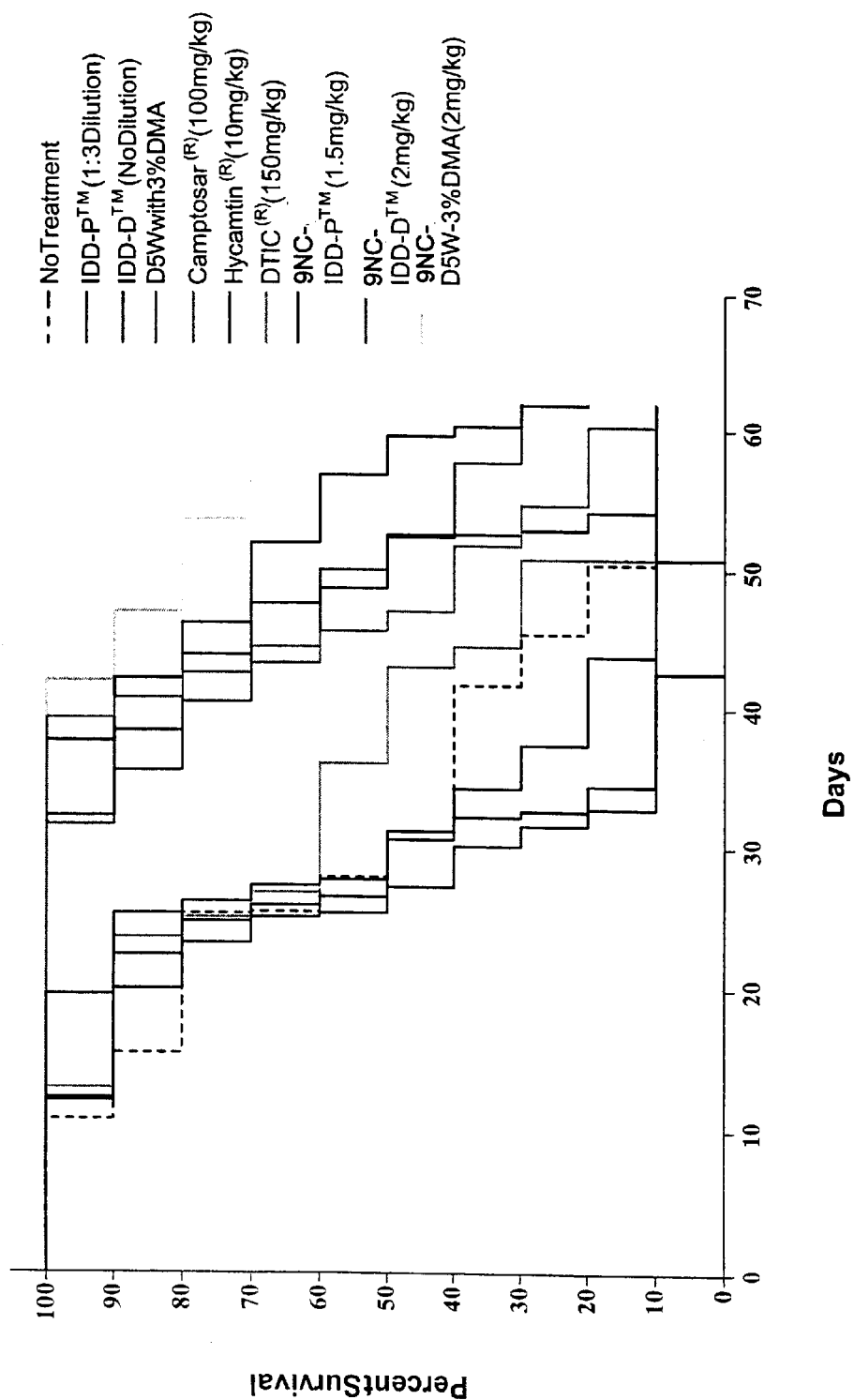
FIG. 9 illustrates survival curves from the first melanoma study.

The particulate 9-nitro-camptothecin suspension in IDD-P appeared to have greater antitumor activity than the droplet suspension in IDD-D. The MDS values were similar for these groups; however, 30% of the Group 9 mice survived at the 1.5 mg/kg dose of 9-nitro-camptothecin in IDD-P while only 20% of the Group 10 mice survived at the higher 2.0 mg/kg dose formulated in IDD-D. Comparison of the survival curves for Groups 9 and 10 in FIG. 9 illustrates the difference in 62-day survival and the somewhat higher mean survival of Group 9, as reflected in the relative position of the curves. Although the absence of any weight loss in mice treated with the IDD-D formulation indicates low host toxicity, the limited solubility of 9-nitro-camptothecin in this vehicle precludes any dose escalation. Therefore, 9-nitro-camptothecin in IDD-P appears to have greater potential as an I.V. antitumor therapy.

Figure 10:
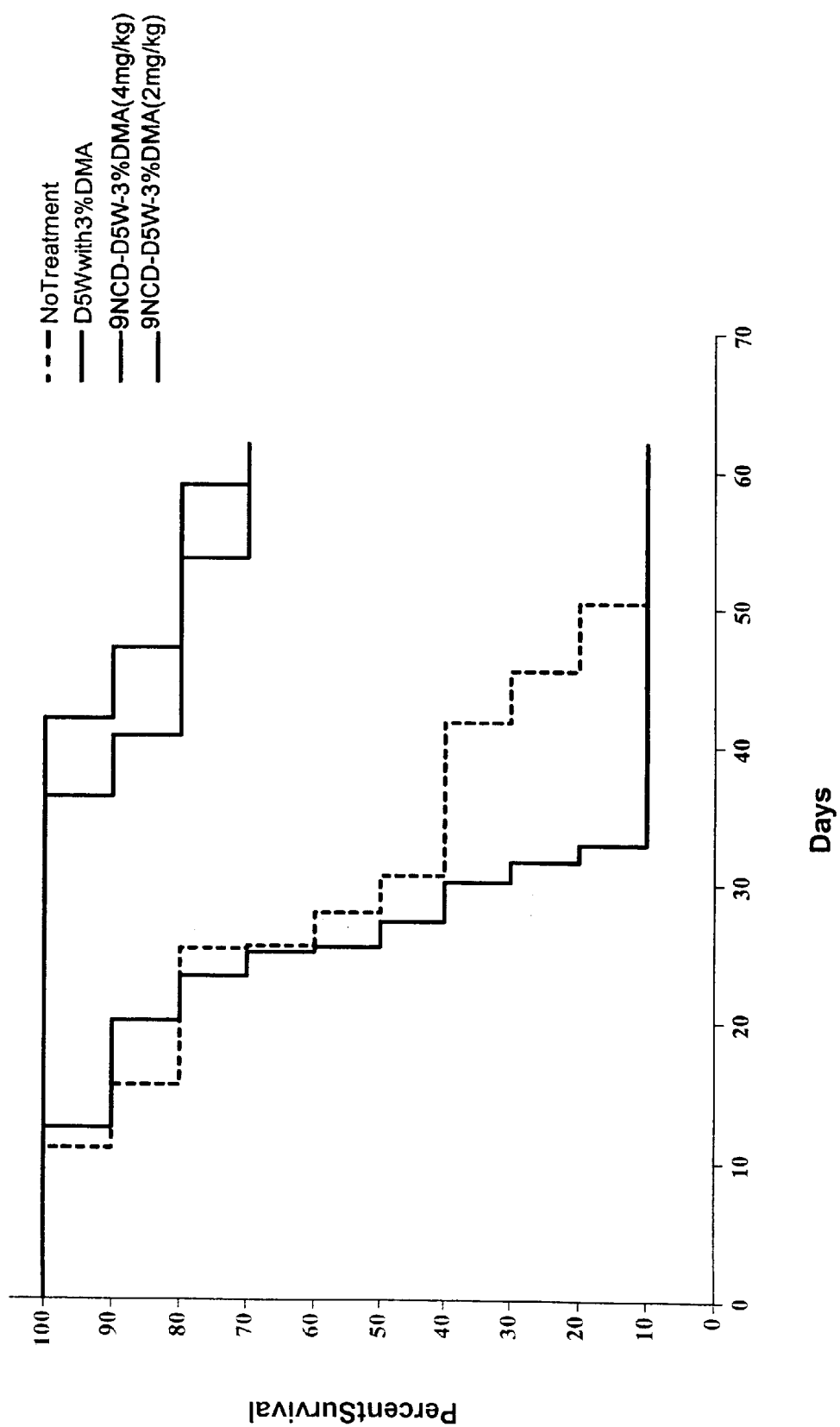
FIG. 10 provides a time to ten-fold growth in tumor size analysis for data from the first melanoma study.
Figure 12B:
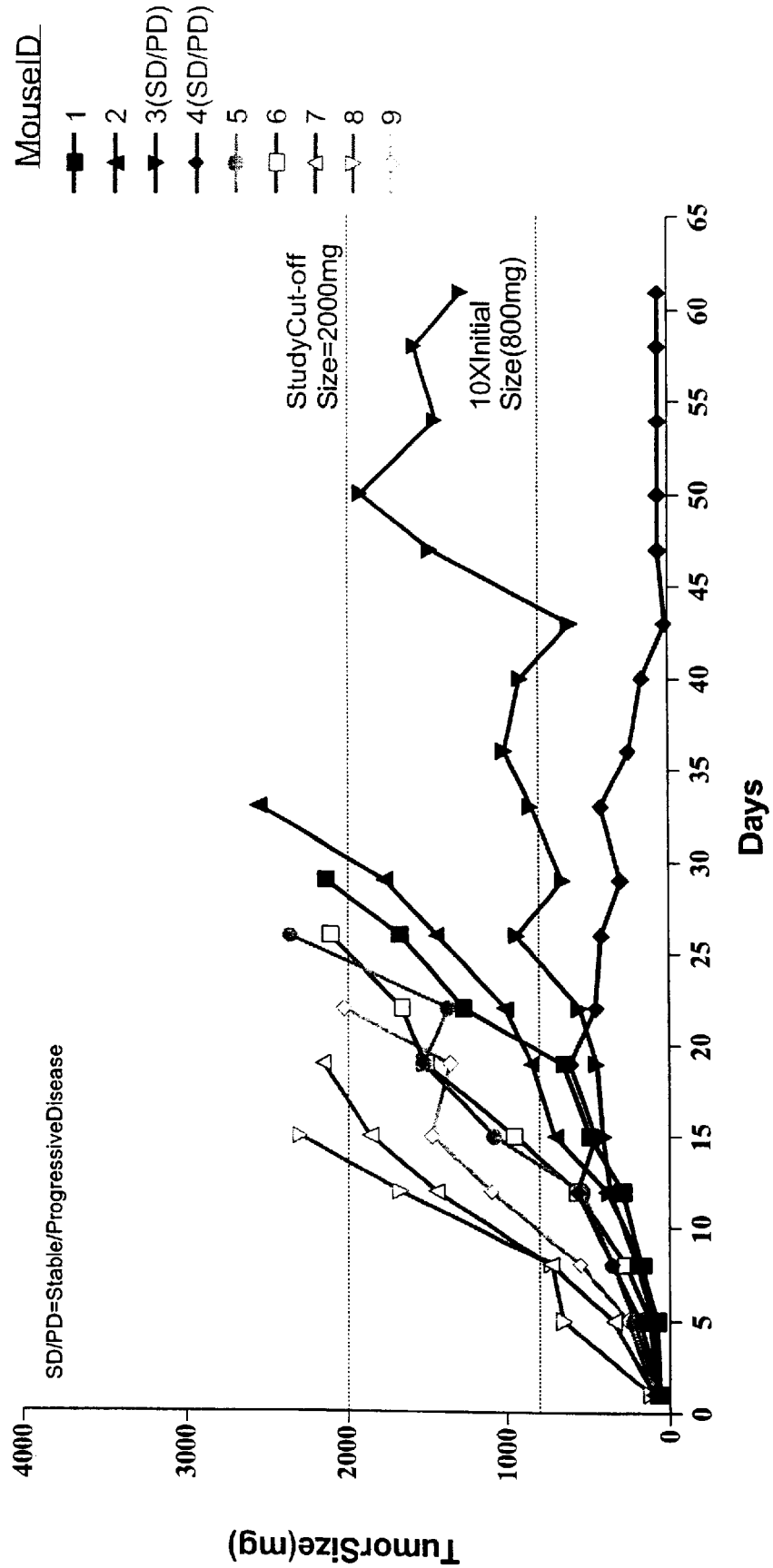
Figure 12C:
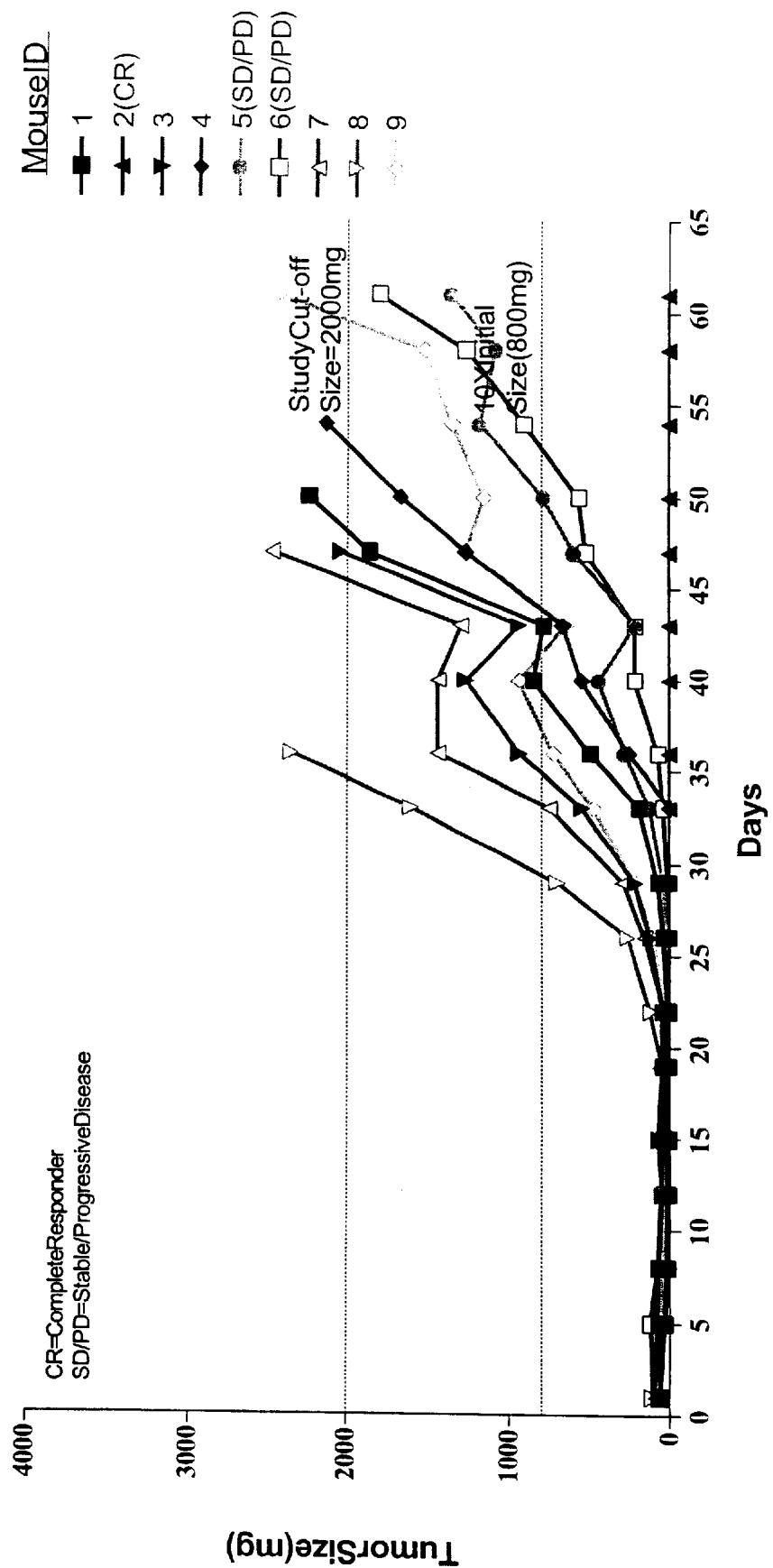
Figure 12D:
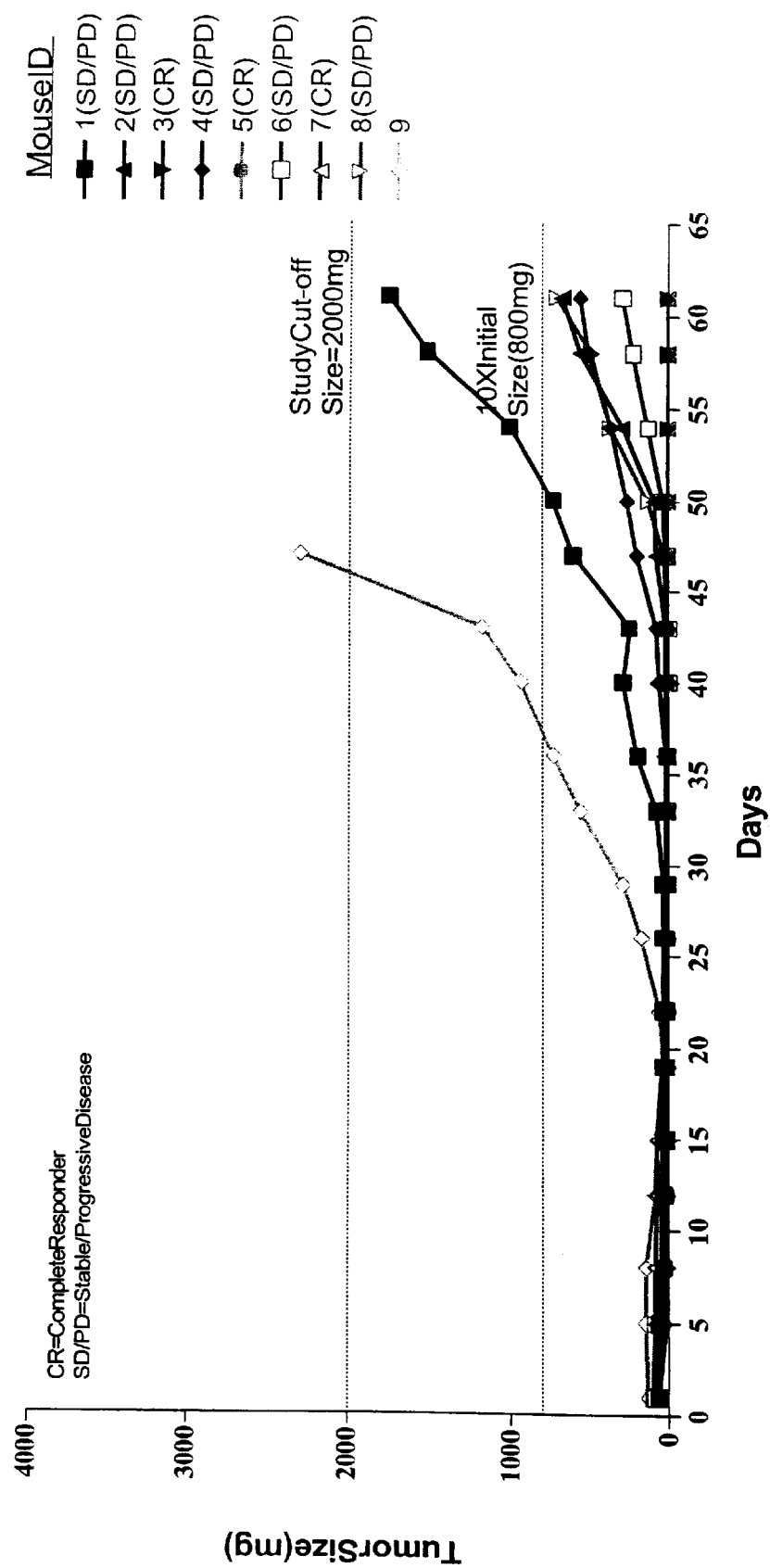

FIG. 10 provides an alternative approach to reviewing and understanding the data collected by this study. This figure summarizes the results of this study in terms of the amount of time (in days) that elapsed before a tumor in a given mouse reached ten times the initial size of the tumor. Since the experiment was conducted for 62 days, if a tumor did not achieve a ten-fold increase in size before 62 days elapsed, a 62 day value was employed.

As can be seen from this figure, a 9-nitro-camptothecin suspension in IDD-P at 1.5 mg/kg was found to be the most effective given its 100% survival rate. IDD-P at 3 mg/kg was also effective but more toxic (70% survival). The 9-nitro-camptothecin suspension in IDD-D was also found to be effective although less effective than IDD-P.

Of interesting note, both the IDD-P and IDD-D formulations were found to be more effective than CAMPTOSAR®, HYCAMTIN®, and DTIC® and were found to be almost as effective as the oral formulation for 9-nitro-camptothecin.

FIG. 10 provides a comparison of therapeutic results achieved with the reference I.P. treatments and the optimal 9-nitro-camptothecin regimen in each vehicle. 9-nitro-camptothecin in IDD-P given on the 5/2/5 schedule at 1.5 mg/kg produced more survivors than CAMPTOSAR® (0% survivors), HYCAMTIN® (0% survivors), and DTIC® (10% survivors), when these reference drugs were given on their optimal regimens. The Kaplan-Meier survival curves for the three reference drugs are positioned to the left of the curve for 1.5 mg/kg 9-nitro-camptothecin in IDD-P. The 1.5 mg/kg I.V. 9-nitro-camptothecin regimen was less effective than 2 mg/kg oral 9-nitro-camptothecin in 3% DMA, even though the I.V. regimen delivered a total dose of 15 mg/kg and the oral dose delivered a total dose of 8 mg/kg. When oral 9-nitro-camptothecin was given q3d×4 at 2 mg/kg or 4 mg/kg, 70% of the mice survived and 40% were CR responses. This difference in survival between Groups 9 and 13 is, however, not statistically significant (P value of 0.1138, log-rank test).

At the 3 mg/kg dose, I.V. 9-nitro-camptothecin produced 50% survivors and provided the longest period of transient tumor suppression seen with any treatment group, but was too toxic. It is possible that a dose above 1.5 mg/kg but below 3 mg/kg could yield stronger therapeutic activity without unacceptable toxicity. Alternatively, an intermittent dosing schedule might allow higher doses of 9-nitro-camptothecin in IDD-P to be administered I.V. without increasing host toxicity. Additional studies are required to determine the optimal schedule for the I.V. administration of 9-nitro-camptothecin in IDD-P formulation. These schedule and dosage issues are being addressed in ongoing studies.

In summary, 9-nitro-camptothecin in IDD-P was a highly effective therapy against human A375 melanoma xenografts in athymic nude mice. On the 5/2/5 schedule, 9-nitro-camptothecin in IDD-P appeared to be superior to the formulation in IDD-D but somewhat less effective than oral 9-nitro-camptothecin in 3% DMA delivered on a q3d×4 schedule.

4. Melanoma Xenograft Model Study 2

The above described study was repeated using another group of mice according to the protocol and conditions as described above regarding study 1. FIG. 11 summarizes the results of this study in terms of the amount of time (in days) that elapsed before a tumor in a given mouse reached ten times the initial size of the tumor. Again, since the experiment was conducted for 62 days, if a tumor did not achieve a ten-fold increase in size before 62 days elapsed, a 62 day value was employed. As can be seen from the figure, the test results of the first study was shown to be largely repeatable. FIGS. 12A–12D provide the individual mouse data from this study.

5. MX-1 Human Breast Cancer Xenograft Study

The following study evaluates the IDD-P formulation against human breast cancer in athymic nude mice. The study used the MX-1 human breast cancer xenograft model to compare the in vivo antitumor efficacy of I.V. 9-nitro-camptothecin, in vehicles containing IDD-P and IDD-D to the efficacy of intraperitoneal CAMPTOSAR® and HYCAMTIN®. Except as indicated in the protocol design for this study, as summarized in FIG. 13, the study was conducted according to the same procedures as specified with regard to the above melanoma study.

In this study, the experiment was conducted for 53 days. If a tumor did not achieve a ten-fold increase in size before 53 days elapsed, a 53 day value was employed.

As can be seen from FIG. 13, IDD-P was shown to be effective in the breast cancer model.

6. Pan c-Human Pancreatic Cancer Xenograft Study

The following study evaluates the IDD-P formulation against pancreatic cancer in athymic nude mice. The study used the Pan c-human pancreatic cancer xenograft model to compare the in vivo antitumor efficacy of I.V. 9-nitro-camptothecin, in vehicles containing IDD-P to the efficacy of intraperitoneal CAMPTOSAR® and HYCAMTIN®. Except as indicated in the protocol design for this study, as summarized in FIG. 14, the study was conducted according to the same procedures as specified with regard to the above melanoma study.

In this study, the experiment was conducted for 58 days. If a tumor did not achieve a ten-fold increase in size before 58 days elapsed, a 58 day value was employed.

As can be seen from FIG. 14, IDD-P was shown to be effective in the pancreatic cancer model.

7. HT-29 Human Colon Cancer Xenograft Study

The following study evaluates the IDD-P formulation against colon cancer in athymic nude mice. The study used the HT-29 human colon cancer xenograft model to compare the in vivo antitumor efficacy of I.V. 9-nitro-camptothecin, in vehicles containing IDD-P to the efficacy of intraperitoneal CAMPTOSAR® and HYCAMTIN®. Except as indicated in the protocol design for this study, as summarized in FIG. 15, the study was conducted according to the same procedures as specified with regard to the above melanoma study.

In this study, the experiment was conducted for 64 days. If a tumor did not achieve a ten-fold increase in size before 64 days elapsed, a 64 day value was employed.

As can be seen from FIG. 15, both IDD-P was shown to be effective in the colon cancer model.

8. SKMES Human Lung Cancer Xenograft Study p The following study evaluates the IDD-P formulation against human lung cancer in athymic nude mice. The study used the SKMES human lung cancer xenograft model to compare the in vivo antitumor efficacy of I.V. 9-nitro-camptothecin, in vehicles containing IDD-P to the efficacy of intraperitoneal CAMPTOSAR® and HYCAMTIN®. Except as indicated in the protocol design for this study, as summarized in FIG. 16, the study was conducted according to the same procedures as specified with regard to the above melanoma study.

In this study, the experiment was conducted for 61 days. If a tumor did not achieve a ten-fold increase in size before 61 days elapsed, a 61 day value was employed.

As can be seen from FIG. 16, both IDD-P was shown to be effective in the lung cancer model.

While the present invention is disclosed by reference to the preferred embodiments and examples detailed above, it is to be understood that these examples are intended in an illustrative rather than limiting sense, as it is contemplated that modifications and combinations will readily occur to those skilled in the art, which modifications and combinations will be within the spirit of the invention and the scope of the appended claims.

What is claimed is:

1. An injectable pharmaceutical composition comprising:
   an aqueous suspension of solid particles suitable for intravenous delivery, the solid particles comprising
   a camptothecin, and
   a 0.3 nm to 3.0 μm thick outer layer comprising a membrane-forming amphipathic lipid that does not tend to form micelle structures;
   wherein the solid particles have mean diameters between about 0.05 μm and 10 μm.

2. An injectable pharmaceutical composition according to claim 1 wherein the camptothecin is selected from the group consisting of 9-nitro-20(S)-camptothecin, 9-amino-20(S)-camptothecin, 9-methyl-camptothecin, 9-chloro-camptothecin, 9-flouro-camptothecin, 7-ethyl camptothecin, 10-methyl-camptothecin, 10-chloro-comptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin.

3. An injectable pharmaceutical composition according to claim 1 wherein the camptothecin is selected from the group consisting of 9-nitro-20(S)-camptothecin, 9-amino-20(S)-camptothecin, 7-ethyl-10-(4-(1-piperdino)-1-piperdino)-carbonyloxy-camptothecin, 7-ethyl-10-hydroxy-20(S)-camptothecin, 10,11-methylenedioxy-20(S)-camptothecin, 9-chloro-20(S)-camptothecin, 9-bromo-20(S)-camptothecin, 9-hydroxy-20(S)-camptothecin, and 11-hydroxy-20(S)-camptothecin.

4. An injectable pharmaceutical composition according to claim 1 wherein the camptothecin is 9-nitro-20(S)-camptothecin.

5. An injectable pharmaceutical composition according to claim 1 wherein the pharmaceutical composition has a pH less than 7.

6. An injectable pharmaceutical composition according to claim 1 wherein the pharmaceutical composition has a pH less than 6.

7. An injectable pharmaceutical composition according to claim 1 wherein the pharmaceutical composition has a pH between 5 and 6.

8. An injectable pharmaceutical composition according to claim 1 wherein the pharmaceutical composition comprises mannitol or trehalose.

9. An injectable pharmaceutical composition according to claim 1 wherein the composition has been thermally sterilized.

10. An injectable pharmaceutical composition according to claim 1 wherein the composition has been thermally sterilized by heating to at least 121° C. for at least 15 minutes.

11. An injectable pharmaceutical composition according to claim 1 wherein the membrane-forming amphipathic lipid comprises a phospholipid.

12. An injectable pharmaceutical composition according to claim 11 wherein the phospholipid is selected from the group consisting of saturated phospholipids, unsaturated phospholipids, synthetic phospholipids, natural phospholipids, and combinations thereof.

13. An injectable pharmaceutical composition according to claim 11 wherein the phospholipid is selected from the group consisting of natural and synthetic lipids, hen egg-derived phospholipid, egg phospholipid, purified egg phospholipid, soy phospholipid, dimyristoyl lecithin, didodecanoyl lecithin, dioeoyl lecithin, dilinoeoyl lecithin, alpha-palmito-beta-oleoyl lecithin, alpha-palmitoyl-beta-linoleoyl lecithin, alpha-oleoyl-beta-palmitoyl lecithin, diarachidonyl lecithin, alpha-palmito-beta-myristoyl lecithin, dimyristoyl phosphatidic acid, dipalmitoyl phosphatidic acid, distearoyl phosphatidic acid, phosphatidyl serine, phosphatidyl inositol, dimyristoyl phosphatidyl glycerol, dipalmitoyl phosphatidyl glycerol, dioctadecanoyl phosphatidyl ethanolamine, dioleoyl phosphatidyl ethanolamine, dihexadecyl phosphatidyl ethanolamine, dilauryl phosphatidyl ethanolamine, dimyristoyl phosphatidyl ethanolamine and dipalmitoyl phosphatidyl ethanolamine.

14. An injectable pharmaceutical composition according to claim 11 wherein the phospholipid comprises egg phospholipid.

15. An injectable pharmaceutical composition according to claim 1 wherein the outer layer further comprises cholesterol.

16. An injectable pharmaceutical composition according to claim 1 wherein the camptothecin is present in amounts of up to about 25% w/w.

17. An injectable pharmaceutical composition according to claim 1 wherein the camptothecin is present in amounts of from about 0.05% w/w to about 5% w/w.

18. An injectable pharmaceutical composition according to claim 1 wherein the camptothecin is present in amounts of from about 0.1% w/w to about 1% w/w.

19. An injectable pharmaceutical composition according to claim 1 wherein the camptothecin is present in amount of about 0.2% w/w.

20. An injectable pharmaceutical composition according to claim 1 wherein the camptothecin is present in amounts of up to about 5% w/w.

21. An injectable pharmaceutical composition according to claim 1 wherein the membrane-forming amphipathic lipid is present in amounts of from 0.2% w/w to about 5% w/w.

22. An injectable pharmaceutical composition according to claim 1 wherein the membrane-forming amphipathic lipid is present in amounts of from 1% w/w to about 5% w/w.

23. An injectable pharmaceutical composition according to claim 1 wherein the membrane-forming amphipathic lipid is present in amounts of about 4% w/w.

24. An injectable pharmaceutical composition comprising:
a dispersion of micrometer to submicrometer size solid particles in an aqueous carrier solution comprising one or more pharmaceutically acceptable tonicity modifier agents, the solid particles comprising
a camptothecin,
a first coating of not more than 10% w/w of a substantially water-insoluble, pharmaceutically acceptable lipophilic agent in which the camptothecin drug is insoluble or poorly soluble, and
a second coating of at least one membrane-forming surface stabilizing amphipathic lipid that does not tend to form micelle structures,
wherein the dispersion does not aggregate, flocculate, or agglomerate, and the particles do not grow in size above a volume weighted mean diameter of 10 μm upon thermal sterilization.

25. An injectable pharmaceutical composition comprising:
a dispersion of micrometer to submicrometer size solid particles in an aqueous carrier solution comprising one or more pharmaceutically acceptable tonicity modifier agents, the solid particles comprising:
a camptothecin, and
a coating of at least one membrane-forming surface stabilizing amphipathic lipid that does not tend to form micelle structures,
wherein the dispersion does not aggregate, flocculate, or agglomerate, and the particles do not grow in size above a volume weighted mean diameter of 10 μm upon thermal sterilization.

26. A pharmaceutical composition suitable for intravenous administration to a manual comprising:
an aqueous suspension of particles having mean diameters between about 0.05 μm and 10 μm, the particles comprising a camptothecin having an intact lactone ring, a membrane-forming amphiphatic lipid coating an outer surface of the particle that does not tend to form micelle structures, and one or more tonicity modifying agents,
wherein the ratio of lipid to camptothecin in the particle is less than about 150:1 moles per mole, and
wherein the mean diameters of the particles increase less than 100% upon thermal sterilization.

27. A pharmaceutical composition according to claim 26 wherein the mean diameters of the particles increase less than 100% upon storage at 23° C. for at least 1 month.

28. A pharmaceutical composition according to claim 26 wherein the mean diameters of the particles increase less than 100% upon storage at 23° C. for at least 3 months.

29. An injectable pharmaceutical composition according to claim 24 wherein the lipophilic liquid vehicle is present in amounts up to about 40% w/w.

30. An injectable pharmaceutical composition according to claim 24 wherein the lipophilic liquid vehicle is present in amounts up to about 25% w/w.

31. An injectable pharmaceutical composition according to claim 24 wherein the lipophilic liquid vehicle is present in amounts up to about 20% w/w.

32. An injectable pharmaceutical composition according to claim 24 wherein the lipophilic liquid vehicle is present in amounts greater than 0.5% w/w.

33. A method according to claim 25 wherein the camptothecin is selected from the group consisting of 9-nitro-20(S)-camptothecin, 9-amino-20(S)-camptothecin, 9-methyl-camptothecin, 9-chloro-camptothecin, 9-flouro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin.

34. A method according to claim 25 wherein the camptothecin is selected from the group consisting of 9-nitro-20(S)-camptothecin, 9-amino-20(S)-camptothecin, 7-ethyl-10-(4-(1-piperdino)-1-piperdino)-carbonyloxy-camptothecin, 7-ethyl-10-hydroxy-20(S)-camptothecin, 10,11-methylenedioxy-20(S)-camptothecin, 9-chloro-20(S)-camptothecin, 9-bromo-20(S)-camptothecin, 9-hydroxy-20(S)-camptothecin, and 11-hydroxy-20(S)-camptothecin.

35. A method according to claim 25 wherein the camptothecin is 9-nitro-20(S)-camptothecin.

36. A method according to claim 26 wherein the camptothecin is selected from the group consisting of 9-nitro-20(S)-camptothecin, 9-amino-20(S)-camptothecin, 9-methyl-camptothecin, 9-chloro-camptothecin, 9-flouro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin.

37. A method according to claim 26 wherein the camptothecin is selected from the group consisting of 9-nitro-20(S)-camptothecin, 9-amino-20(S)-camptothecin, 7-ethyl-10-(4(1-piperdino)-1-piperdino)-carbonyloxy-camptothecin, 7-ethyl-10-hydroxy-20(S)-camptothecin, 10,11-methylenedioxy-20(S)-camptothecin, 9-chloro-20(S)-camptothecin, 9-bromo-20(S)-camptothecin, 9-hydroxy-20(S)-camptothecin, and 11-hydroxy-20(S)-camptothecin.

38. A method according to claim 26 wherein the camptothecin is 9nitro-20(S)-camptothecin.

* * * * *